United States Patent
Macgregor et al.

(10) Patent No.: US 8,131,020 B2
(45) Date of Patent: Mar. 6, 2012

(54) METHOD FOR CONTROLLING THE APPEARANCE OF PRODUCTS AND PROCESS PERFORMANCE BY IMAGE ANALYSIS

(75) Inventors: John F. Macgregor, Dundas (CA); Jay J. Liu, Hamilton (CA)

(73) Assignee: McMaster University, Hamilton, Ontario (CA)

( * ) Notice: Subject to any disclaimer, the term of this patent is extended or adjusted under 35 U.S.C. 154(b) by 1160 days.

(21) Appl. No.: 11/596,429

(22) PCT Filed: May 18, 2005

(86) PCT No.: PCT/CA2005/000768
§ 371 (c)(1),
(2), (4) Date: Sep. 7, 2007

(87) PCT Pub. No.: WO2005/114338
PCT Pub. Date: Dec. 1, 2005

(65) Prior Publication Data
US 2008/0013821 A1    Jan. 17, 2008

Related U.S. Application Data

(60) Provisional application No. 60/572,467, filed on May 20, 2004.

(51) Int. Cl.
*G06K 9/00* (2006.01)
(52) U.S. Cl. ......... 382/110; 382/170; 382/190; 382/208
(58) Field of Classification Search ............. 382/224, 382/110, 170, 190–208, 155–160
See application file for complete search history.

(56) References Cited

U.S. PATENT DOCUMENTS

| | | | |
|---|---|---|---|
| 2,689,043 A * | 9/1954 | Fischer | 209/166 |
| 5,878,153 A * | 3/1999 | Mikulec et al. | 382/108 |
| 6,587,575 B1 * | 7/2003 | Windham et al. | 382/110 |
| 6,778,881 B1 * | 8/2004 | Du Plessis et al. | 700/265 |
| 7,068,817 B2 | 6/2006 | Bourg, Jr. et al. | |
| 2003/0065462 A1* | 4/2003 | Potyrailo | 702/81 |
| 2003/0208496 A1* | 11/2003 | Xing | 707/100 |
| 2004/0031005 A1* | 2/2004 | Yunoki | 716/8 |
| 2004/0091135 A1* | 5/2004 | Bourg et al. | 382/110 |
| 2004/0197012 A1* | 10/2004 | Bourg et al. | 382/110 |

(Continued)

OTHER PUBLICATIONS

Panjwani, D.K.; Healey, G., Markov random field models for unsupervised segmentation of textured color images, Oct. 1995, Mentor Graphics Corp., Wilsonville, OR, IEEE Transactions on Pattern Analysis and Machine Intelligence, vol. 17 Issue:10, p. 939-954.*

(Continued)

*Primary Examiner* — Aaron W Carter
(74) *Attorney, Agent, or Firm* — Steven M. Greenberg, Esq.; Carey Rodriguez Greenberg & O'Keefe, LLP

(57) ABSTRACT

A new application of machine vision for process industries is proposed. The invention consists of: (1) estimation of visual quality of products, (2) modeling causal relationship between estimated quality and process variables, and (3) optimization of visual quality using the causal model. This invention can handle the stochastic nature in visual appearance of products that process industries provide, which has been a main obstacle for the success of machine vision in process industries. Also, it opens new tasks in machine vision such as modeling and optimization of visual quality of products.

16 Claims, 35 Drawing Sheets

U.S. PATENT DOCUMENTS

| | | | |
|---|---|---|---|
| 2005/0149889 A1* | 7/2005 | Messerman et al. | 716/3 |
| 2006/0041851 A1* | 2/2006 | Gallatin et al. | 716/4 |
| 2008/0013821 A1* | 1/2008 | Macgregor et al. | 382/141 |
| 2009/0283146 A1* | 11/2009 | Lambert | 137/1 |
| 2010/0082149 A1* | 4/2010 | Till et al. | 700/214 |

OTHER PUBLICATIONS

Horst et al., "Machine Vision System for Precision Dimensional Measurements and On-Line SPC", Coference Record of the 1989 Industry Applications Society Annual Meeting, Oct. 1-5, 1989.*

* cited by examiner

"Too many clear windows"   "Good froth"   "Close to collapsing"

840

511

630

245

19

413

| Current image | Desired image | Achieved image |
|---|---|---|
| 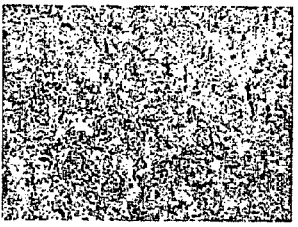 |  | 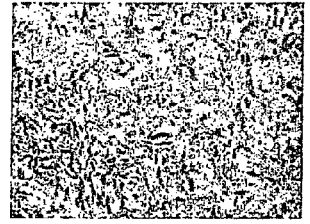 |
| $y = [2.23\ 2.73]^T$ | $y = [0.03\ 1.50]^T$ | $y = [0.20\ 1.66]^T$ |
| FIG 5A | FIG 5B | FIG 5C |
| Current image | Desired image | Achieved image |
| 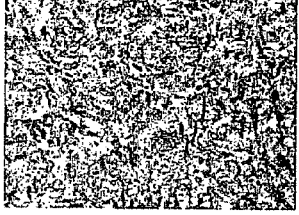 | 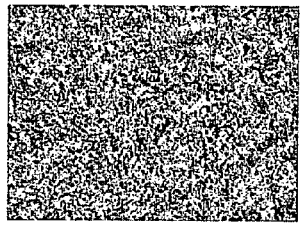 | 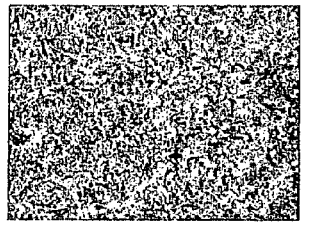 |
| $y = [-0.37\ 1.06]^T$ | $y = [2.90\ -1.34]^T$ | $y = [2.96\ -1.32]^T$ |
| FIG 5D | FIG 5E | FIG 5F |

211

373

800

273

293

318

323

338

348

I074  I183  I243  I283

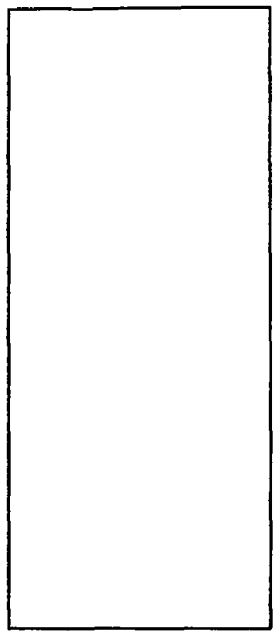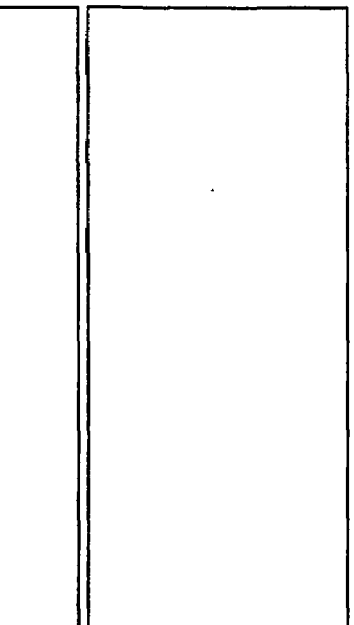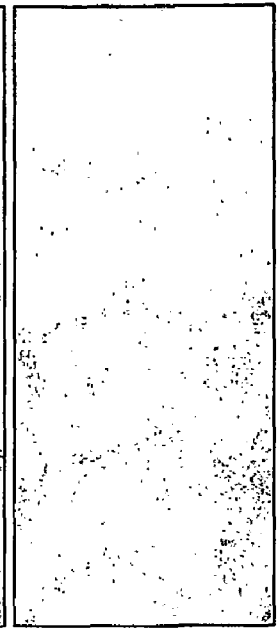
0.222        0.431        0.415        0.466
FIG 22A              FIG 22B
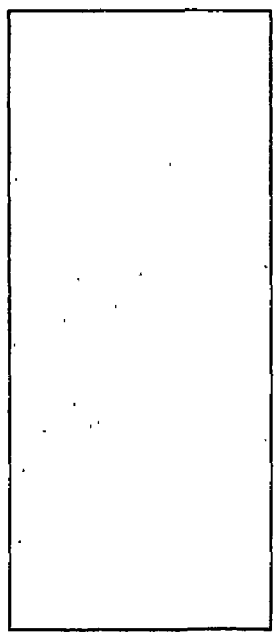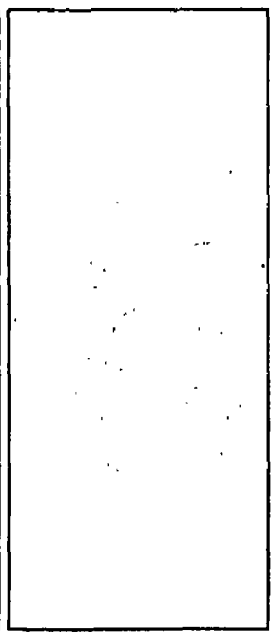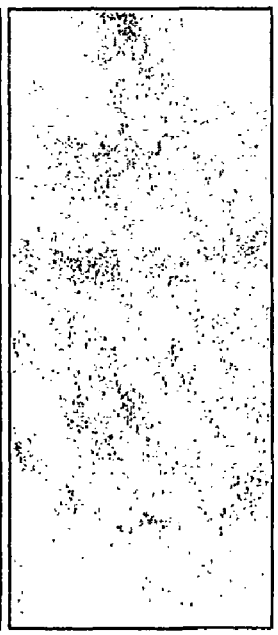
0.078        0.141        0.398        0.418
FIG 22C              FIG 22D

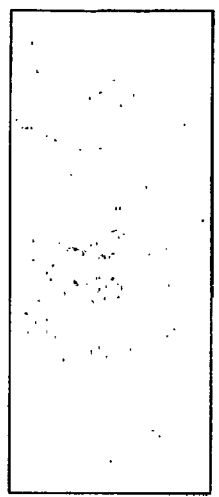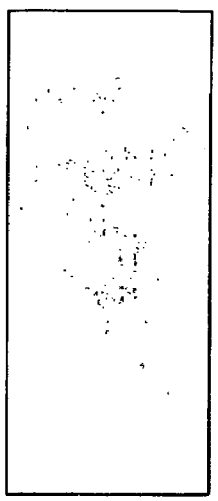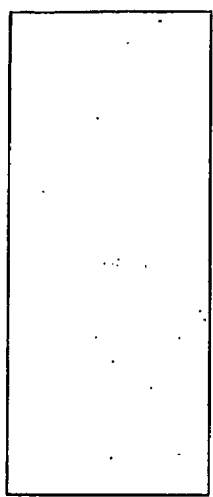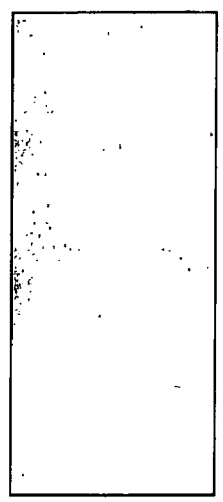
I123　　　　　　I138　　　　　　I089　　　　　　I059
FIG 27

Table 1

| Dimension of Latent Space | $R^2$ | $Q^2$ |
|---|---|---|
| 1 | 0.928 | 0.916 |
| 2 | 0.971 | 0.943 |
| 3 | 0.987 | 0.958 |
| 4 | 0.995 | 0.970 |

FIG. 31

Table 2
| Target quality (I074) | Predicted Quality |
|---|---|
| $y=[-5.917\ 0.349\ 0.115\ 0.271]^T$ | $\hat{y}=[-4.291\ 0.013\ -0.096\ 0.188]^T$ |
| Conditions = [1 F4 P1] | Optimized conditions = [2.2 F5 P3] |
| 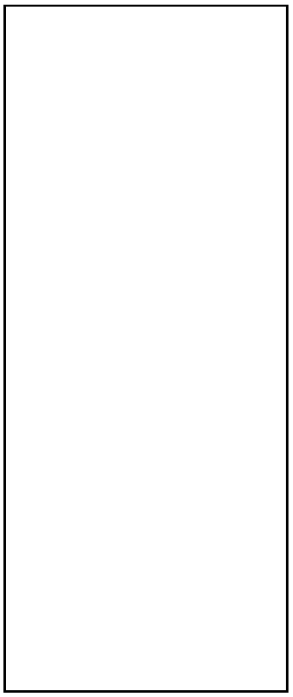 | 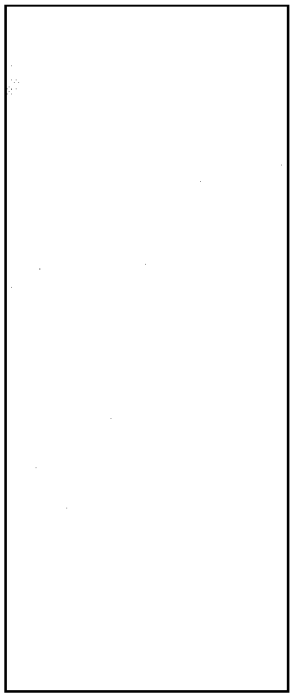 |
FIG. 32

Table 3
| Target quality (1133) | Predicted Quality |
|---|---|
| $y=[2.716\ 1.982\ -0.221\ -0.376]^T$ | $\hat{y}=[2.225\ 1.941\ -0.344\ -0.194]^T$ |
| Conditions = [2 F1 P4] | Optimized conditions = [2.2 F1 P3] |
| 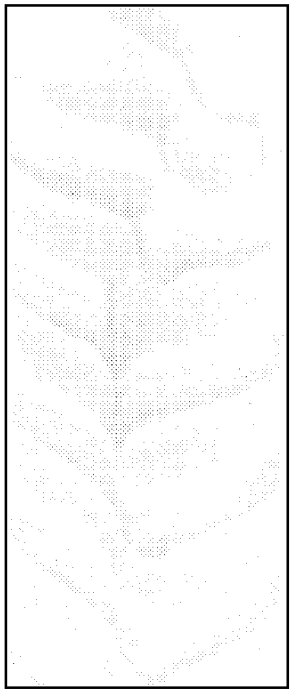 | 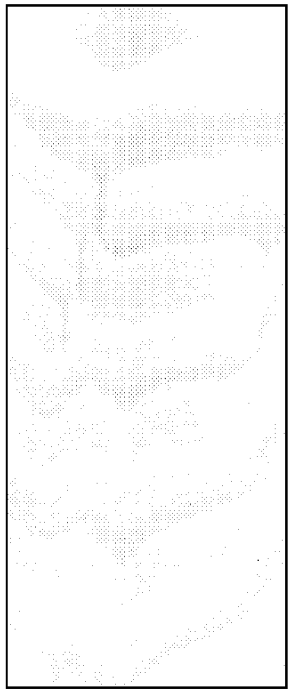 |
FIG. 33

Table 4

Table 5
| Target quality (I243) | Predicted Quality |
|---|---|
| $y=[-1.275\ -1.001\ -0.133\ -0.159]^T$ | $\hat{y}=[-1.267\ -0.890\ -0.071\ -0.124]^T$ |
| Conditions = [2 F4 P2] | Optimized conditions = [1.81 F5 P5] |
|  |  |
FIG. 35

METHOD FOR CONTROLLING THE APPEARANCE OF PRODUCTS AND PROCESS PERFORMANCE BY IMAGE ANALYSIS

TECHNICAL FIELD

This invention relates to the application of machine vision to industrial processes in order to optimize the quality of a resulting product or improve efficiency of the underlying process.

BACKGROUND ART

Machine vision has been studied for about 40 years but the study in last 15 years has shown drastic progress due to the great advances in imaging and computing technologies. The main purpose of machine vision is to allow a computer to understand aspects of its environment using information provided by visual sensors. The subject of machine vision now embraces innumerable topics and applications: these range from automatic assembly and inspection to automatic vehicle guidance, from automatic documents interpretation to verification of signatures, and from analysis of remotely sensed images to checking of fingerprints and recognizing faces, to list just a few.

Automatic inspection and assembly is one of the areas where machine vision has been most successfully applied and it is still showing substantial growth. The necessity of improvements in quality, safety, and cost saving is the reason driving this growth. However, most successful techniques and their applications in this area have been confined to a specific type of environment where certain assumptions can be made about the scene. In typical manufacturing industries such as microelectronics fabrication for example, an image provides a scene of objects with pre-determined shape, structure, orientation, and so on, unless the position of a camera changes. In other words, images from such industries are deterministic. The primary goal of the inspection in such manufacturing industries is to check whether there are missing objects in pre-specified regions in the image or whether objects in the image are in desired orientations, and the necessary analysis is mainly done in image space.

An object of this invention is to provide a new field of application for machine vision to process industries. In this invention, machine vision will include new application areas and new tasks that have seldom been tried in contemporary machine vision research. New application areas include all process industries where the stochastic visual appearance of products or processes is a major concern. New tasks include estimation, modeling, control, and optimization of visual quality of the process or the product. Visual quality include textural appearance of processes and products. However, it can include spectral (i.e., color) and/or textural appearance of products and methodologies combining these two aspects have been proposed [MR-MIA].

DISCLOSURE OF INVENTION

In accordance with the invention, there is provided a method for optimizing appearance in a characterizing product of an industrial process which is influenced by process variables, the method comprising the steps of:
  capturing digital images of the characterizing product
  extracting information from the images to create a feature vector
  performing multivariate statistical analysis on the feature vector to obtain latent variables which characterize the image
  performing a regression analysis to build a model to correlate the latent variables with said process variables and creating a control algorithm for calculating changes in said process variables required to obtain desired appearance qualities in the characterizing product.

The method according to the invention may be performed to identify an initial setting for process control variables in an industrial process, for off-line monitoring and control of process variables, or performed on-line to monitor and control process variables.

The images defining the appearance of the characterizing product may be captured in any selected region of the electromagnetic spectrum and may be grayscale images, or captured in the visible or near infra-red spectrum.

In accordance with one of its aspects, a multivariate statistical projection method is applied to an image to reduce the dimensions to a low dimensional score space image data defined by a small number of score vectors $t_a$ and the feature vector is created from the low dimensional score space image data.

Depending on the field of the application, the multivariate statistical projection method is selected from the following; multi-resolution analysis (MRA) based on 2-dimensional wavelet transforms, multivariate image analysis (MIA) based on principal component analysis (PCA), or combinations thereof, Markov Random Field (MRF), Gabor filters, and variations thereof.

The applications for which the invention are suitable include optimizing and controlling flotation froth in industrial mineral flotation processes, in particular froth flotation of zinc concentrate and zinc concentrate, optimizing surface quality of plastic injection molded materials; and creating suitable formulations for the production of artificial counter tops.

The invention also provides a novel way of extracting spectral and textural information from multispectral images by combining multi-resolutional analysis based on wavelets or spatial filters and Multivariate Image Analysis based on Principal Component Analysis (MR-MIA) as well as a novel way of summarizing the appearance of images by principal component (PC) score values of the extracted features and displaying as PCA score plots.

BRIEF DESCRIPTION OF DRAWINGS

The invention is described below with reference to the accompanying drawings, in which:
FIGS. 5A-5F show control simulation results.

FIGS. 22a-22d two nearest neighbors of the three images shown in FIG. 19 and corresponding Mahalanobis distances to the images in FIG. 19A I263 and I268 for I 74 FIG. 19B I198 and I188 for I183 FIG. 19C I267 and I278 for I243 FIG. 19D I293 and I288 for I283;

FIG. 27 four selected images in the $t_3$-$t_4$ score plot;

FIG. 31 contains Table 1, which is a summary of principal component analysis;

FIG. 32 contains Table 2, which shows optimization results for I074. I064 is the nearest neighbor of ŷ. Mahalanobis distance between y and ŷ is 0.958;

FIG. 33 contains Table 3, which shows optimization results for I133 as a target quality. I128 is the nearest neighbor of ŷ. Mahalanobis distance between y and ŷ is 0.737;

FIG. 35 contains Table 5, which shows optimization results for I243 as a target quality. I278 is the nearest neighbor of ŷ. Mahalanobis distance between y and ŷ is 0.262.

BEST MODE FOR CARRYING OUT THE INVENTION

Figure 1:
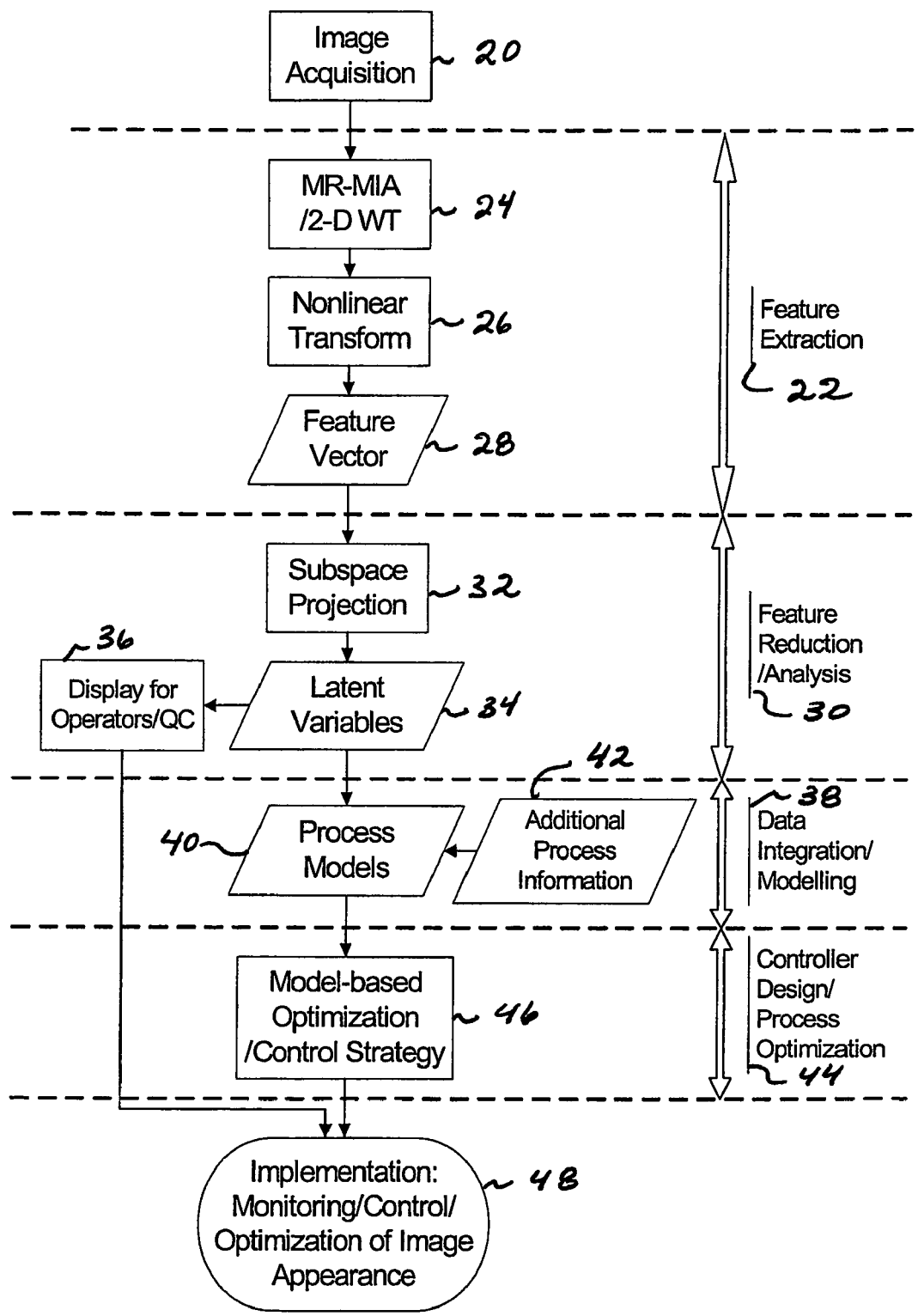
FIG. 1 is a work flow diagram showing the invention.

A schematic flowchart illustrating the steps of the invention is shown in FIG. 1. The reference numerals following each heading correspond to the reference numerals of FIG. 1

Image Type and Acquisition 20

Images can be of several types, any of which can be used for the control/optimization of appearance. Choice will depend only on what type of imaging is necessary to capture the important appearance characteristics. For example, grayscale images can be used, as in the injection molding of plastic parts where only the visual appearance related to flow lines in the product is important. If some important features of visual appearance relate to color, as in the artificial countertop manufacturing process, and in the mineral flotation process, then color (RGB) (red green blue) images are needed. If chemical variation throughout a product is important such as in polymeric coatings or films, but cannot be visually seen, then a Near-Infrared (NIR) imaging spectroscope can be used to obtain changing "chemical appearance" throughout the image.

The images can either be acquired frequently on-line (as in the mineral flotation example described later) or less frequently off-line in a quality control laboratory (as in the counter top and plastic parts examples described later). In the former case, this allows the methodology to be used for rapid on-line control and optimization of the appearance of the process or product appearance. In the latter case this allows for finding optimal design conditions for the process and for occasional control actions to keep product appearance in control.

Feature Extraction 22

The purpose of this is to extract the important textural and color (spectral) information from the images. The digital images consist of several megabytes of data giving spectral/color information at every pixel location in the image. The extracted features should summarize all the important textural and color information in the image in terms of a much smaller number of features. In the flotation process this consists of bubble size distribution information obtained from MRA (Multiresolution Analysis) and the area of clear windows/holes in the froth obtained from MIA (Multivariate Image Analysis). In the injection molding of plastic parts and in artificial countertop manufacturing, this consists of the variance of wavelet coefficients in different detail images obtained from MRA and of spectral (color) information extracted by specific MIA masks. This column of features that summarizes the important information in the image problem is referred to as the feature vector.

The preferred methodology for capturing the important spectral/color and textural information in an image is Multi-resolution Analysis (MRA) based on 2-dimensional wavelet transforms 24—including Discrete Wavelet Transform (DWT) and Wavelet Packets (WP), and multivariate image analysis (MIA) based on Principal Component Analysis (PCA). These methodologies can be combined in two ways; MR-MIA I where MRA is applied to each color (or wavelength) channel and then MIA applied to a newly formed multivariate image at each resolution. MR-MIA II where MIA is first applied and then MRA applied to each score images selected. Details of methodology are contained in the accompanying examples.

However, other methodologies could be used by those skilled in the art to extract information that could be used for calculating a feature vector 28. For textural information, these include Markov Random Field (MRF) and its variations, various filtering methods such as Gabor filters, etc. For color information, these include other ways of extracting specific color information such a simple thresholding in different color bands or masking in the IHV space of RGB images.

Feature Reduction/Analysis 30

The purpose of feature analysis is to further simplify and condense the feature vector 28 information into a smaller number of features that present all the important information in the feature vector in a more efficient manner. The preferred methodologies used here are PCA and other multivariate statistical methods 32.

The result of this analysis are a smaller number of orthogonal principal component scores 34 ($t_1, t_2, \ldots$) that summarize all the important textural and spectral information in the images. Images whose visual appearance (with respect to the important textural and spectral features) is almost identical will have score values (values of $t_1$ $t_2, \ldots$) that are almost identical or at least fall very close together (cluster) in the same region of a score plot of $t_1$ vs. $t_2$, etc. (see Figure of the examples). This fact can be used to cluster and classify images of similar appearance according to their PCA score values. This allows for displaying score plots (e.g., $t_1$ vs. $t_2$) to the operators 36 so that they can see within what cluster or class the current image falls. It allows the appearance of every image to be summarized by a small number of score values ($t_1, t_2, \ldots$). In flotation processes, this provides the operators with an immediate measure of the state or health of the froth by observing the location of the ($t_1, t_2$) scores in the score plot. This step also provides the basis for the crucial element of this patent application, namely controlling the visual appearance of an entire image by indirectly controlling the principal component score values ($t_1, t_2, \ldots$).

Process Modeling/Data Integration 38

The purpose of this step is to build a model 40 that shows how changes in the manipulated variables of the process (x's) (e.g. the reagent flows in flotation, the injection speed in plastic parts manufacturing) or changes in the recipe formulation variables (z's) (e.g. the amounts of all ingredients in the polymer formulation for the plastic parts) will affect the score values of the principal components ($t_1, t_2, \ldots$). In other words, a model of the form $t_i = f(x_1, x_2, \ldots; z_1, z_2, \ldots)$, (i=1, 2, ...) is built. With this relationship, one then has a model that will predict how changes in these process/formulation variables will affect the PC score values of the images and hence how indirectly it will affect the appearance of the images. To build this model, one generally needs additional information 42 from the process in the form of deliberate or "designed" changes in the process and formulation variables (a designed experiment) and the images of the process or product that result from them. Some form of regression analysis (multi-variable linear regression, partial least squares regression, artificial neural networks, etc.) is then used to build a model relating the "independent" process and formulation variables to the principal component scores ($t_1, t_2, \ldots$) that characterize the resulting image.

Controller Design/Process Optimization 44

The purpose of this step is to use the model 40 developed between the PC scores ($t_1, t_2$) and the independent process and formulation variables to design a control algorithm or optimization algorithm 46. The control algorithm 46 can be based on any existing model-based control theory. The result is that for a specified target (or desired values) of the principal component scores ($t_1,sp, t_2,sp, \ldots$), the control algorithm will compute changes in values of the independent process and/or formulation variables which will move the process from its current status (given by the PC scores for the current image) to values close to the desired target values. The key concept in this image appearance control methodology is that by controlling the values of the PC scores to desired values, one is indirectly controlling the appearance of the entire image of the process or product. This indirect control of the appearance of images by controlling a small number of score values ($t_1, t_2, \ldots$) is the heart of the invention.

The same concept holds for process optimization. However, in optimization rather than computing the adjustments in the process and formulation variables necessary to move the process to desired values (e.g., flotation), values of these independent variables are computed (subject to constraints and limits on them) which will give the most desirable values of the PC scores within a given region, and hence the most desirable appearance.

Implementation of Control/Optimization 48

Depending upon the availability of images and the automation level of the plant, one can implement the control/optimization over the textural and spectral appearance of the process or the product in different ways (given below in increasing order of sophistication);

(i) One time optimization of process and formulation conditions: The injection molding of plastic parts provides a useful illustration of this method. In the development of the process in a pilot plant or in a new full-scale plant, the methodology is used to find those settings of the process variables and formulation variables which will yield the best appearance of the product for different applications. These conditions will then be implemented for production. (An example of this is the injection molding process for the production of plastic parts with a specified surface appearance.)

(ii) Off-line monitoring and control of appearance: This is a classical statistical quality control (SQC) or statistical process control (SPC) problem. An example is the SPC or SQC of appearance in the manufacture of artificial countertops. The final product is prepared and imaged periodically in the quality control lab. Its PC score values (t1, t2) are plotted either on individual control charts (e.g., Shewhart charts) or as multivariate control charts (Hotelling's T2, etc.). Control limits are established for action. If the score values from the images lie within the acceptable region of the control chart, no action is taken. (This implies that these images fall within acceptable range of appearances.) If the PC score values fall outside of the control limit, this implies that something has occurred which makes the appearance unacceptable. The action can be either to investigate what has happened and correct it, or to compute an adjustment to the process variables or formulation variables that will bring the scores back to desired target values (thereby returning the product to an acceptable appearance.)

(iii) On-line control of process/product appearance: This is the classic feedforward/feedback control problem. Images are collected on-line in real time, and processed to give their PC score values. These values are compared to the desired values or set-points for these scores and the process variable or formulation changes are computed and implemented to bring the process/product image scores back to these desired values. In the most automated plants this can be done using process computers and control actions computed and implemented every few seconds or minutes. In other situations these control actions can simply be presented to the operators as suggested actions to be implemented if they feel an adjustment is necessary. Either of these scenarios is feasible in mineral flotation processes to control the froth appearance.

SUMMARY OF INDUSTRIAL APPLICATIONS

Example 1

Figure 2:
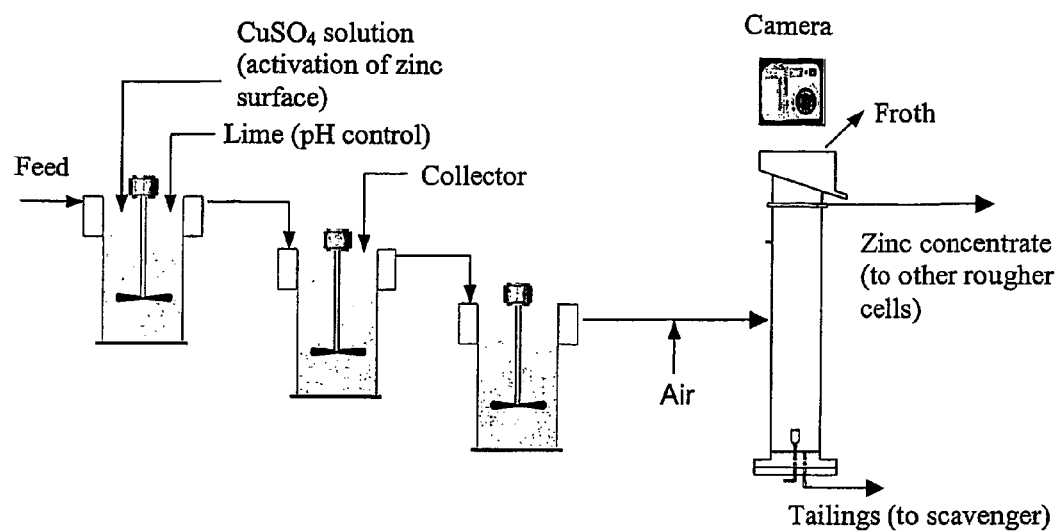
FIG. 2 is a schematic diagram of process and image acquisition.
Figure 3A:
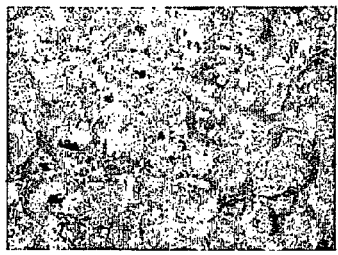
FIGS. 3A, 3B, 3C show froth images and corresponding status assessed by operators.
Figure 3B:
Figure 3C:
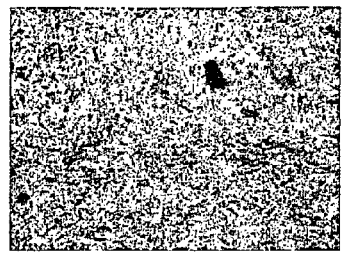

Control of Flotation Froth Appearance/Health in Industrial Mineral Flotation Process FIG. 2 is a schematic process diagram of part of Agnico-Eagle's Laronde plant in Quebec, Canada. The camera was installed on top of the flotation column. It samples 24-bit, 720'480 (width'height) color images at every minute. The manipulated variables include pH level, froth level, air flow rate, CuSO4 flow rate, and collector flow rate. Currently, operators change some of these manipulated variables by observing and assessing froth status. Typical froth status described by operators is shown in FIG. 3.

Image Acquisition 20

RGB images collected every 30 sec by an automated imaging system.

Feature Extraction 22

Features used by the operators for the basis of the assessment are clear windows (see the image in the left above), black holes (see the image in the right above), and bubble size distribution. Using MR-MIA, a wavelet size signature analysis is used to extract information related to the distribution of froth bubble sizes and MIA masks are used to extract the number of pixels belonging to clear windows/black holes from each new image. The observed values of all these features are collected into a feature vector associated with each image.

Feature Reduction/Analysis 30

After PCA on feature vectors consisting of these features the variation of froth status can be modeled by two principal components 34 ($t_1$ and $t_2$) as shown in FIG. 4.

Similarity/dissimilarity of the froth status of different images is well represented by their position in the score plot above. Images with almost identical appearance have score values falling very close to one another in the score plot. Images with very different appearance have widely separated score values.

Process Modeling/Data Integration 38

The appearance or health of the froth can be affected by manipulating process variables (x's—reagent flowrates, etc.) and feed ore conditions (z's). A causal model 40 is developed via regression that can predict the PC score values ($t_1$, $t_2$) and hence the froth appearance from changes in those variables (x, z). Dynamic models or steady-state models are built depending on the nature of the control implementation desired. The general form of such causal models is $\hat{y}=f(x,z)$ where $y=[t_1\ t_2\ldots]^T$. As an illustration a steady-state model is built using steady-state data from regions SS1, ss2 and SS3 in FIG. 4 by performing Partial Least Squares regression of the score values $t_1$ and $t_2$ from PCA of feature vectors of froth images against one manipulated variable $x=x_m$ ($x_m$=FIC426A_SP), and feed conditions, z. The table below shows that 84.5% of the variation in the scores can be explained and 74.7% of the variability is predictable for scores from new images not used in the model building.

Steady-state plant model: $\hat{y} = f_{PLS}(x, z)$, where $y = [t_1\ t_2]^T$.

| A | $R_x^2$(cum) | $R_y^2$(cum) | $Q_y^2$(cum) |
|---|---|---|---|
| 1 | 0.316 | 0.597 | 0.551 |
| 2 | 0.612 | 0.755 | 0.701 |
| 3 | 0.799 | 0.809 | 0.727 |
| 4 | 0.903 | 0.845 | 0.747 |

Controller Design/Process Optimization 44

Control of visual froth status can be done based on inversion of steady-state model via optimization. For linear PLS models with A latent dimension, new manipulated variables $\hat{x}$ for achieving desired froth status $y_{sp}=[t_{1,sp}\ t_{2,sp}\ldots t_{A,sp}]^T$ are given as $[\hat{x}^T\ \hat{z}^T]=\hat{u}^TP^T$ where $\hat{u}$ is a solution of the following optimization problem;

$$\hat{u} = \arg\min_u \|y_{sp} - \hat{y}\|^2$$
$$s.t.\ u^T S_u^{-1} u \le c_1\ \text{and}\ |z - \hat{z}| \le c_2 1,$$

where $\hat{y}^T = u^T Q^T$. P and Q are matrices from linear PLS equations $X=UP^T+E$ and $Y=UQ^T+F$, and rows of X and Y matrices consist of past values of $[x^T\ z^T]$ and $[t_1\ t_2\ldots t_A]$, respectively.

Alternatively, algorithms for implementing control actions based on slightly different objectives can be equally well formulated, as is well known by those in the field.

Implementation 48

Figure 6:
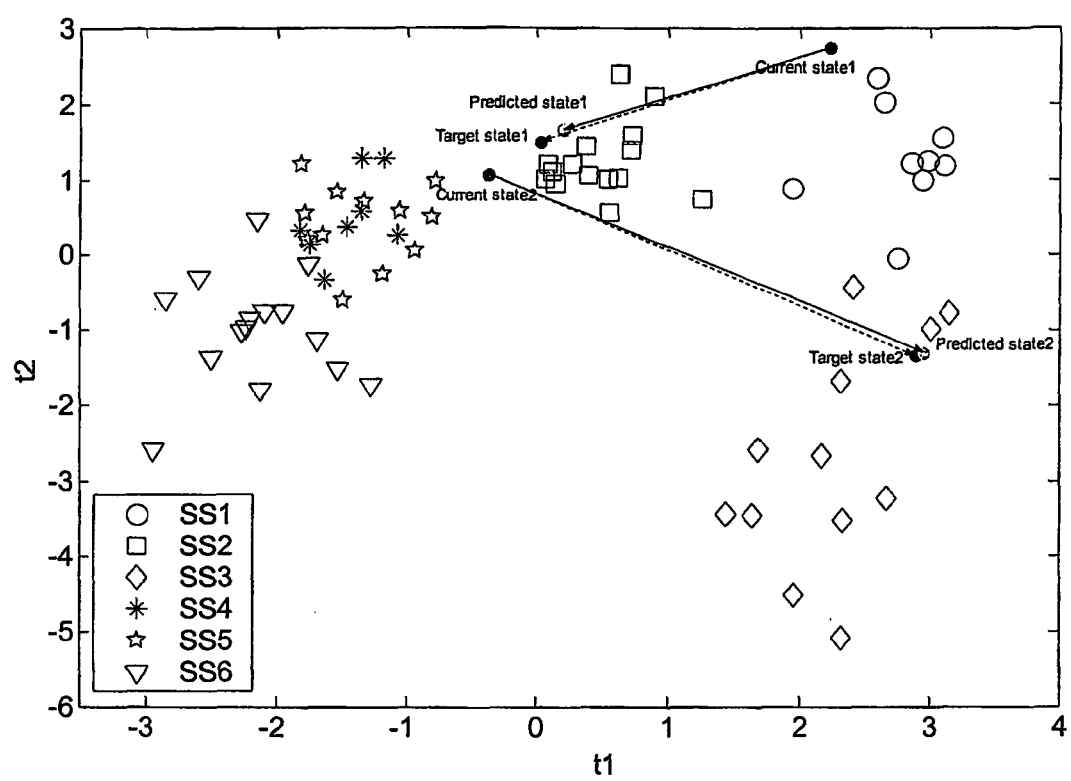
FIG. 6 shows control simulation results in the score plot.

Based on the PLS model, and the control algorithm above new values of the manipulated variable which are needed to change froth status to desired targets are calculated and compared to real data in FIGS. 5 and 6. In FIG. 5 the current froth image with score values given by $y=[2.23\ 2.73]^T$ (see FIG. 6) shows too heavy a loading and it is desired to change its appearance to that shown on the right with score values $y=[0.03\ 1.50]^T$. Given the currently observed values of the feed variable (z), the control algorithm computed that a change in the reagent flow ($x_m$) to a value of 4.63 is needed and gave the image shown in the right bottom part of FIG. 5 with score values of $y=[0.20\ 1.66]^T$. Note that the appearance and score values of the image achieved is almost identical to that desired. This movement achieved by the control algorithm is shown in the PCA score plot as move 1 in FIG. 6.

A second control move is also illustrated in FIGS. 5 and 6 where the current froth image with score values given by $y=[-0.37\ 1.06]^T$ shows a healthy froth and we deliberately try to change its appearance to that shown on the right with score values $y=[2.90-1.34]^T$ (a froth on the verge of collapsing). Given the currently observed values of the feed variable (z), the control algorithm computed that a change in the reagent flow ($x_m$) to a value of 6.78 is needed and gave the image shown in the right bottom part of FIG. 5 with score values of $y=[2.96-1.32]^T$. Note that the appearance and score values of the image achieved is almost identical to that desired. This movement achieved by the control algorithm is shown in the PCA score plot as move 2 in FIG. 6.

Example 2

Optimization of Plastic Parts in an Industrial Injection-Molding Process

Image Acquisition 20

Grayscale images were collected off-line in a QC laboratory.

Feature Extraction 22

After performing a 5 level discrete wavelet transform the standard deviations of the sub-images were calculated as features.

Feature Reduction/Analysis 30

Figure 7:
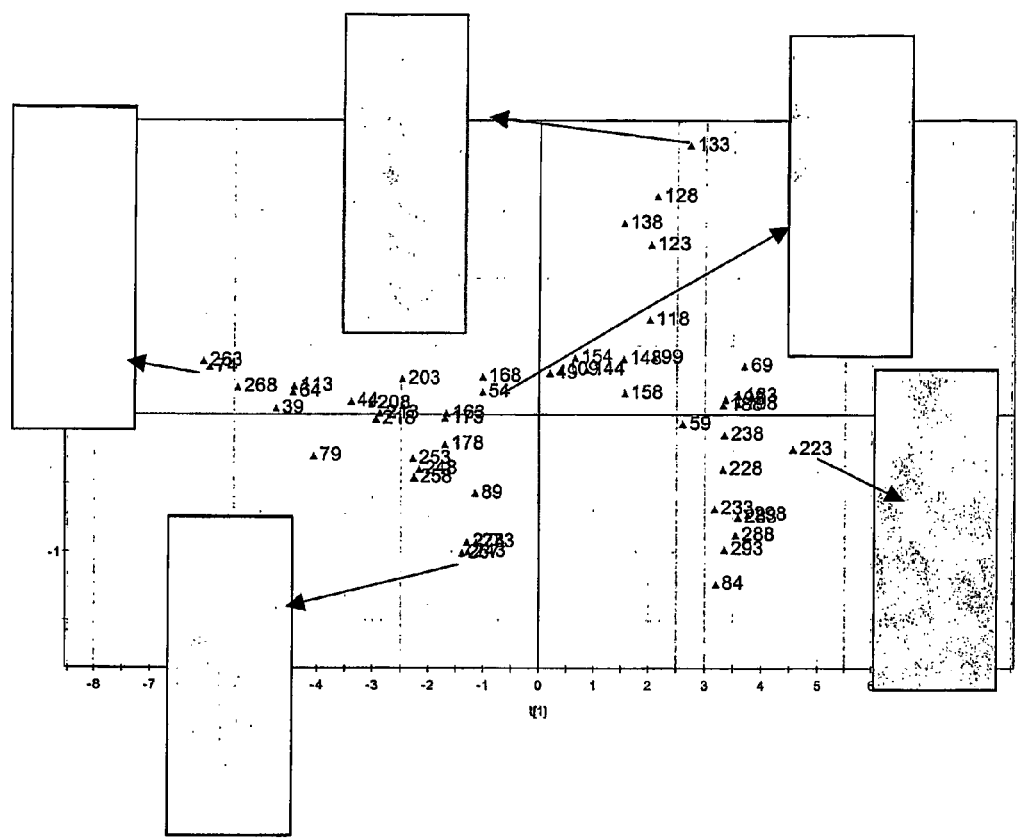
FIG. 7 is a $t_1$-$t_2$ score plot.
Figure 8:
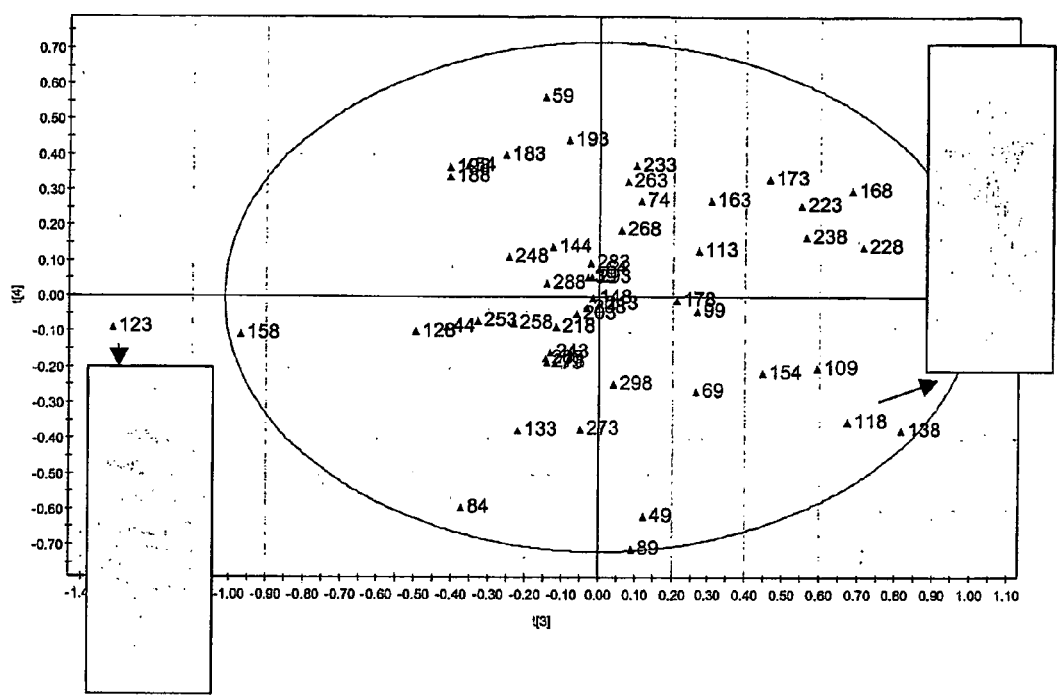
FIG. 8 is a $t_3$-$t_4$ plot.

Performing a PCA on the feature vectors from the images shows four significant principal components PCs. Based on the t1-t2 score plot in FIG. 7 and the t3-t4 plot in FIG. 8 interpretations of four PCs are as possible; (1) t1 represents presence of any visible patterns in the images, (2) t2 represents presence of structured (horizontal, vertical, and diagonal) wave patterns, (3) t3 represents presence of vertical (positive direction) wave patterns, and (4) images in the negative t4 direction have low intensity and vertical wave patterns.

Process Modeling/Data Integration 38

Figure 9:
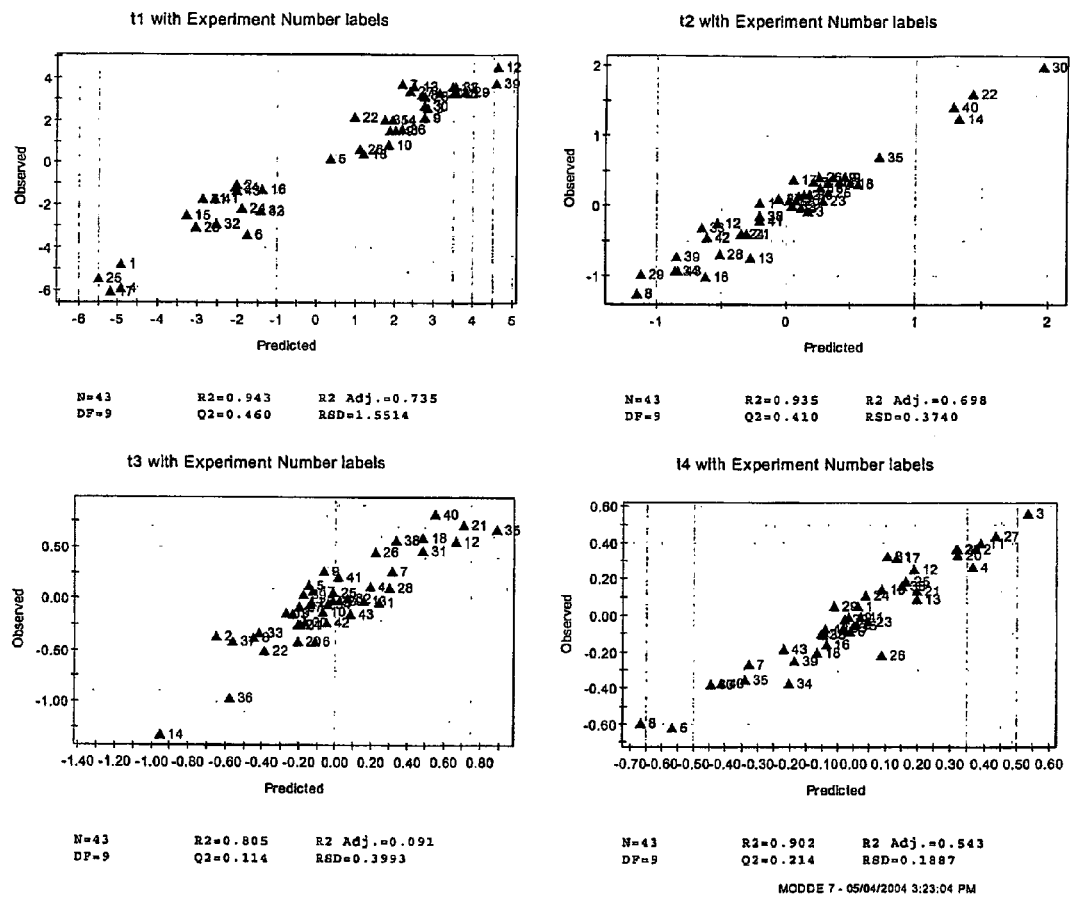
FIG. 9 shows control simulation results.
Figure 10:
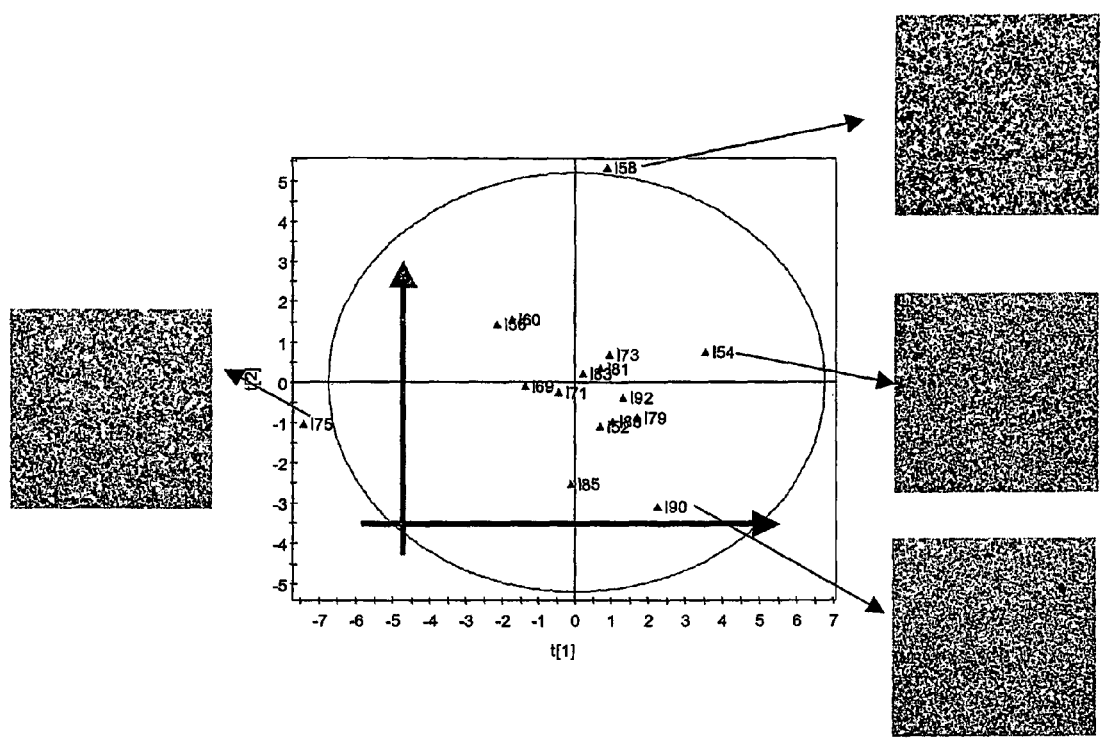
FIG. 10 is a $t_1$-$t_2$ score plot.

A linear PLS model is built using three operating conditions as x-variables and $[t_1\ t_2\ t_3\ t_4]^T$ as y-variables. Results of observed versus predicted sores $(t_1, \ldots, t_4)$ in FIG. 9 show that a good model is obtained.

Controller Design/Process Optimization 44

The PLS model can be used for (1) process optimization, i.e., finding operating conditions to achieve desired visual quality and (2) batch-to-batch control (or adjustment).

Example 3

Quality Control of Appearance in Manufacture of Artificial Countertops

Image Acquisition 20

Color images were collected off-line at the quality control QC laboratory for different products (1) a black and white countertop—discussed below, and a brown, white, grey and black one.

Feature Extraction 22

After performing a 5 level discrete wavelet transform (DWT), the energies of each sub-image were calculated as features.

Feature Reduction/Analysis 30

Performing a PCA on the feature vectors of the images shows three significant PCs and interpretation of four PCs are as follows; (1) t1 captures fineness (or coarseness) in the images, (2) t2 captures contrast in the images, and (3) t3 captures patterns with more clear edges.

Currently, pre-determined operating conditions are used for every product grade and final products are imaged and analyzed periodically in the quality control lab. An imaging system in the laboratory would enable monitoring the quality of the countertops by plotting control charts on $t_1$, $t_2$ and $t_3$.

In addition operators adjust operating conditions by manually observing the image of a product a short time after the start of a new production run. This mid-course correction to the process could be done automatically by the image control methodology presented in this document.

DETAILED DESCRIPTION OF INDUSTRIAL APPLICATIONS

Control of Flotation Froth in Mineral Flotation

The flotation process is one of the most widely used separation processes in mineral processing (in particular for sulphide ores) to separate valuable metals from ore. Although many studies have been devoted to it, the chaotic nature of the underlying microscopic phenomena related to surface chemistry and surface physics makes it very difficult to monitor and control flotation processes through fundamental modeling approaches. In addition, reliable on-line sensors are not available to provide measurements that are essential for automatic monitoring and control. This paper investigates a novel approach to using digital imaging for monitoring flotation processes.

It is widely known that color and morphology of the froth are closely related to mineral concentrations and process status, respectively. As a consequence, many operational changes are made by operators based on visual appearance of the froth together with their experience. For these reasons, over the past decade image analysis has been considered as a potentially key component to the monitoring of flotation processes.

The object of this aspect of the invention is to provide a novel solution to the characterization and monitoring of the flotation froth based on multiresolutional multivariate image analysis (MR-MIA). By combining multiresolution analysis (MRA) and multivariate image analysis (MIA), it is possible to analyze the spatial and spectral correlation of images within a single framework. The approach based on MR-MIA is totally different from the contemporary image research in the sense that it handles morphological and color information of froth images efficiently. In addition, this approach is inherently robust to image quality or lighting conditions, contrary to most contemporary image analysis approaches.

Visual Features of Froth and Extraction Methods

Color and structure of flotation froth are very important visual features in the operation of a flotation process. Color is strongly related with the type of minerals carried by the froth. The structure of the froth, that is its texture or morphology (bubble size, distribution and, shape, etc.) is known to indicate various froth characteristics such as degree of mineralization (froth load), stability, and so on, although the relationship between mineral concentration and froth structure is not clear. Operators usually determine the rate of addition of chemical reagents (i.e., control inputs or manipulated variables) based on those visual features of the froth.

Image analysis based on traditional image processing techniques has been applied to flotation processes in order to monitor the process or to infer mineral concentrations. For estimating mineral concentration, statistical features like mean, standard deviation, skewness, and kurtosis are calculated from each RGB (red, green, blue) color channel, and then multiple linear regression or PLS partial least squares) are used to construct an inferential model. It is reported that no significant differences are detected using either bubble domain or the full image color approaches. HSI (Hue, Saturation, Intensity) or HSV (Hue, Saturation, Value) color models other than RGB model are used in some cases in order to overcome high collinearity among R, G, and B values. In HSI or HSV color models, the intensity component, I, or the brightness value, V, is decoupled from the color information in the image. In addition, bubble collapse rate, bubble mobility (speed), and various morphological features (froth bubble size, shape, etc.) are extracted via traditional image analysis methods and used in regression, but the results fail to show the relationship to mineral concentration clearly; whereas the variance of froth mobility and the bubble collapse rate show some correlation to zinc concentration, but the correlation of mineral concentration with morphological features is lower than that obtained with color features.

The analysis of froth structure has frequently been carried out using segmentation methods, texture analysis methods, and Fourier transform (FT) power spectrum. Morphological features such as bubble diameter, aspect ratio, etc. are calculated for each bubble after segmentation of the froth images into bubbles and then used in estimating mineral concentration. One of the popular segmentation methods used is the watershed algorithm. Many other image-processing techniques are used to enhance the quality of image prior to segmentation. Statistical texture analysis methods such as gray-level co-occurrence matrix (GLCM) and its variations, and fractal analysis are used to classify the status of different froths based on froth texture in order to monitor flotation processes. Power spectrum from 1-D or 2-D Fourier transform (FT) is also used to extract textural features of the froth.

It is clear from the literature that the correlation structure among the color in the RGB images has not been considered in most cases. Although HSI and HSV models have sometimes been used in some cases, they are rather basic approaches to handling the collinearity. Lighting condition is also crucial in analyzing color features but efforts made for removing the effect of different lighting or illumination have been so heuristic or ad-hoc that they could not be easily generalized. In this respect, MIA based on Principal Component Analysis (PCA) provides a better approach than others that have been used in the literature since PCA can easily handle the collinearity. Furthermore, it was experimentally verified that some features (e.g., energy and entropy) calculated after applying PCA to color images were illumination-invariant as long as intensity saturation did not occur. This invariance property is extremely important for image analysis in real applications since lighting conditions often change and are often beyond our control. Wavelet texture analysis (WTA) has been considered as the state of the art in texture analysis for many reasons. It outperforms other methods such as GLCM-based methods or FT-based methods and is much more computationally efficient and robust to lighting conditions than segmentation-based methods. Therefore, MR-MIA would appear to offer an excellent alternative to contemporary image analysis approaches for monitoring and controlling flotation processes. MR-MIA combines advantages of MIA and multiresolution analysis; it can handle high collinearity in RGB froth images more efficiently than HSI and HSV models and can extract structural feature of froth in a faster and more robust manner than segmentation-based or GLCM-based approaches. An overview of MR-MIA methods for extracting color and structural information from froths is discussed in the next section.

Visual Feature Extraction Using MR-MIA 22

As mentioned earlier, there seems no strong correlation between mineral concentrations (i.e., color information) and froth morphology and thus one can analyze them separately. Therefore, the MR-MIA II algorithm is more preferable in this situation since in MR-MIA II spatial information and spectral information are extracted and processed separately as follows;

Algorithm: MR-MIA II
(i) Apply PCA to the original multivariate image (a RGB image in this article) and determine an appropriate number of principal components.
(ii) Apply multiresolution decomposition on each PCA score image.

Figure 11:
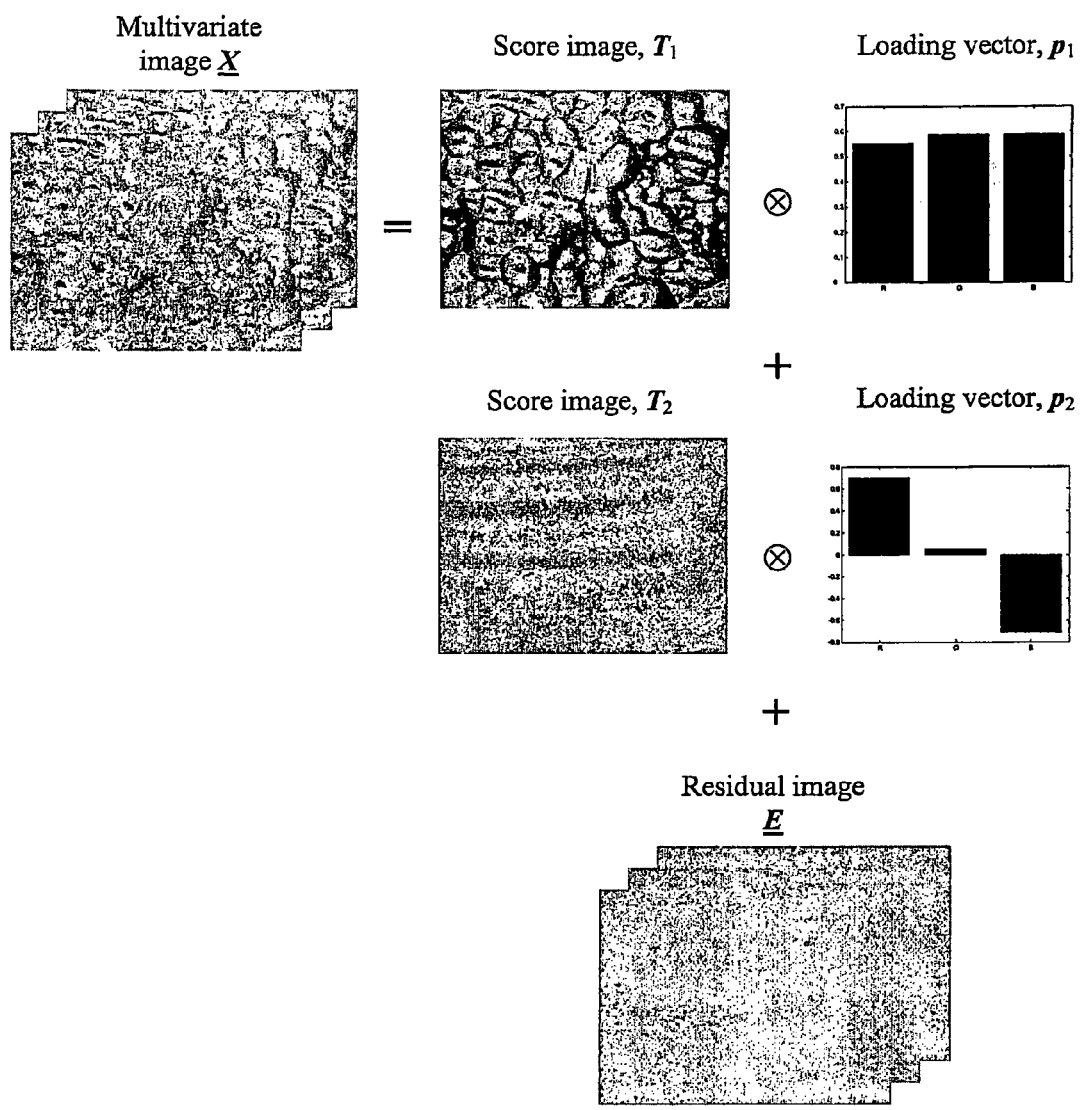
FIG. 11 is an illustration of Multivariate Image Analysis using the RGB images shown in FIGS. 3A-3C.

Color features will be extracted in the PCA stage of MR-MIA II and then morphological features will be calculated from WTA of the first score image, which it is almost equivalent to the grayscale version of a RGB image in most cases (for example, see $T_1$ and $p_1$ in FIG. 11).

The purpose of image analysis in flotation froth analysis is to extract features that can indicate the status of the process and thus can be used for process monitoring and control. Some of the features may be common to the flotation of other mineral systems, but others are not. This is because each plant can show some unique characteristics depending on the flotation cell used, the mineralogy of the ore, etc. Furthermore, visual features are clearly subjective, and even operators in the same plant may have different criteria when interpreting the images. Therefore, we based our work on interviews about froth visual features with operators and engineers at the plant (Agnico-Eagle's Laronde plant in Quebec, Canada) where the froth image collection was performed.

Clear Windows and Black Holes

A clear window is a watery portion of the froth, found on the top of the bubbles, that has almost no mineral content (see FIG. 3). Therefore, froths with many clear windows usually have big bubbles, and are usually an indication that the degree of mineralization in the froth is very low. The color of the clear window is much darker and blacker than other regions such as the tops and valleys of the froth, thus sometimes they are called black windows and have often been seen in zinc flotation cells. It is one of three major visual features of froth that operators at Laronde plant use to determine the state of their operations. When froths are too lean, operators usually increase collector or activator usage to increase mineral loadings. On the other hand, one can find black holes when froths are excessively loaded with minerals (see FIG. 3). A Black hole is a portion of froth surface, which is so close to the pulp that the pulp can be seen through it. Black holes usually appear when bubbles are extremely small and often provide a warning that the entire froth may collapse.

However, these features have never been used for monitoring of flotation processes in the literature. Extracting clear windows and black holes can be easily done using masking in multivariate image analysis (MIA) since it extracts spectral (i.e., color) features independent of their spatial location. The total areas (i.e., a number pixels) of clear windows and black holes are then easily extracted. The only difficulty is that clear windows and black holes are spectrally similar (i.e., similar colors), and hence difficult to distinguish by MIA alone.

Calculating Area of Clear Windows and Black Holes Using MIA Masks

A RGB color image is a simple example of a multivariate image, which is defined as a set of congruent univariate images forming in a three-way array of data, with two dimensions being geometrical coordinates, and the third dimension the spectral coordinate. A multivariate image, $\underline{X}(N \times K \times Q)$ is a stack of Q($N \times K$) images and can be decomposed using PCA as $$\underline{X} = \sum_{a=1}^{A} T_a \otimes p_a + \underline{E} \qquad (1)$$

where under-bar '_' indicates three-way array, $T_a(N \times K)$ are score matrices, $p_a(Q \times 1)$ are loading vectors, $\otimes$ is Kronecker product and $\underline{E}(N \times K \times Q)$ is a residual array. Equation (1) is illustrated in FIG. 11 using the image shown in FIG. 3.

Figure 12A:
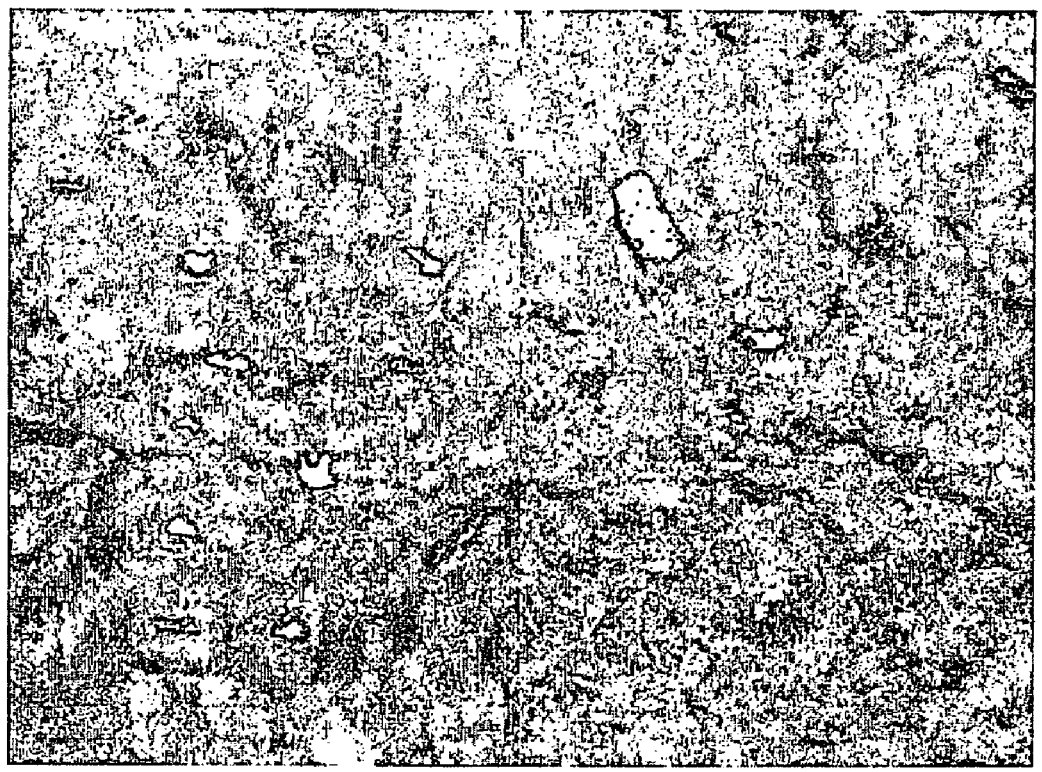
FIG. 12A The composite multivariate image from the images in FIGS. 3A-3C a $t_1$-$t_2$ score plot of the composite image with the boundary of clear windows and black holes highlighted in white. Clear windows and black holes found by the boundary are highlighted in white in FIG. 12A.
Figure 12B:
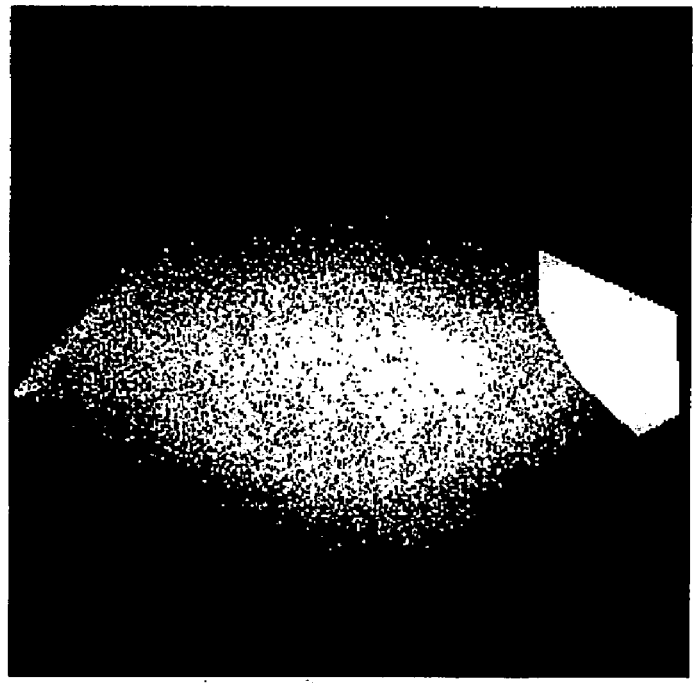
FIG. 12B is a hot colormap from MATLAB® used to represent a 2-D histogram of score plot.

A density score plot is obtained by plotting the same elements in score matrices using their values as new coordinates. A density score plot is one of major analysis tools of MIA since it reveals clusters, trends, outliers, and similarity between pixels. Pixels having very similar spectral features lie close to one another in the score plots, regardless of their positions in the image space and such score plots can be thought as two-dimensional histograms if they are segmented into a number of bins in each of the score dimensions. An example of a scatter score plot is shown in FIG. 12(a) for the image in FIG. 3 where the brightness of each point indicates the number of pixels falling within a bin in the score plot. We can detect different features in the original image space using a scatter score plot by defining a mask or a feature boundary for each feature as determined from a training image, because the coordinate of each pixel in the score plot is uniquely determined by its variable correlations. The number of pixels within the feature boundaries represents the area of these features in the image space. A feature boundary is usually found by interactive inspection between such score plots and the original image. Because clear windows and black holes are spectrally similar the composite image was made from portions of the images in FIG. 3 and shown in FIG. 12(a). The feature boundary for clear windows and black holes for the composite image is shown in FIG. 12(b) and pixels falling inside the boundary are highlighted in FIG. 12(a).

Froth Bubble Size

Froth bubble size is one of the most commonly used morphological features throughout the literature and it is another major feature used by operators at the Laronde plant for characterizing process status. In fact, the measurement of bubble size has been of great interest in the mining process industry since it has been extensively reported that the performance of a flotation process is strongly related to the size.

Considerable effort has been made for calculating bubble size. Probably the most accurate way is based on segmentation. Using segmentation techniques, one can find a size (an equivalent diameter, lengths of major and minor axes, etc.) of a bubble, count the number of bubbles, and calculate a histogram of bubble size from them. The biggest problem in using segmentation techniques in practice however is that segmentation is too sensitive to lighting conditions and to the segmentation techniques used and in addition it is computationally demanding compared to other alternatives. Therefore, segmentation techniques are not suitable for providing fast and reliable estimation of the size of froth, which is essential for any image analysis technique to be accepted by industries. These are reasons why the majority of commercial machine vision systems for flotation froth don't use segmentation techniques to calculate the size of froth.

On the other hand, it has been also reported that the froth texture is a strong indicator of process performance. This is because froth structure (shape, size, etc.) is one of the textural constituents by definitions of texture. For this reason, statistical texture analysis techniques such as gray-level co-occurrence matrix (GLCM) and its variants (e.g., texture spectrum and neighboring gray-level difference matrix (NGLDM)) have been used to classify froth images into predefined classes that correspond to different process status. Also, fractal analysis and FFT power spectrum have been used in the same context. These approaches seem robust to lighting conditions due to the inherent robustness of statistical texture analysis techniques. However, it is difficult to characterize actual froth structure or morphology by using textural features calculated using these methods; textural features are not directly related to froth structure or morphology such as bubble size. Therefore several attempts have been made to find textural features that are strongly correlated to froth structure and to regress them with (manually) measured froth structure. However, they failed to provide an adequate description of froth structure because they could produce an estimate of an average bubble size only, not the bubble size histogram. The MR-MIA II approach proposed in this paper will be shown to provide a direct estimate of the size histogram of bubbles while maintaining a lower computational cost and better robustness to lighting conditions compared to the previous approaches based on segmentation or statistical texture analysis techniques.

Calculating Histogram of Froth Bubble Size Using Wavelet Size Signature

Wavelet theory deals with the study of time- or space-frequency behavior of functions or signals (Because we deal with two-dimensional signals (i.e., images), we will use the word space instead of time). Since its first use for texture analysis in the early 90's, texture analysis based on wavelet theory, which is now widely known as wavelet texture analysis (WTA), has been considered as the state of the art among other texture analysis methods not only because wavelet analysis can be implemented very efficiently using filter banks also because there is strong evidence that the human visual system does indeed perform some sort of multi-channel, space-frequency analysis. Furthermore, it is reported that WTA has shown better performance than other methods in many cases and that WTA is more robust to changes in lighting conditions than other texture analysis methods such as GLCM.

A basic idea of WTA is to extract a textural feature from wavelet coefficients at each resolution and assume that each texture has its unique distribution of features over all the resolutions. Therefore, different textures will have different features if the frequency spectrum is decomposed appropriately. Typical textural features in WTA are energy, entropy, or averaged $l_1$-norm. However, these WTA features have the same problem; they have no morphological meaning. For this reason, we develop a new feature, calculated from the WTA features, called wavelet size signature, which can provide a histogram of bubble size.

Space-Frequency Representations and Uncertainty Principle

In wavelet decomposition, a signal f(x) is decomposed in terms of a family of orthonormal bases $\psi_{m,n}(x)$ obtained through translation and dilation of a mother wavelet $\psi(x)$, i.e., $$\psi_{m,n}(x) = 2^{-m/2}\psi(2^{-m}x - n) \qquad (2)$$

where m, n are integers. Due to the orthonormal property, the wavelet coefficients then can be defined as the convolution of the signal with these wavelet bases:

$$c_{m,n} = \int_R f(x)\psi_{m,n}(x)dx = <\psi_{m,n}(x), f(x)>. \qquad (3)$$

In other words, wavelet coefficients are measures of the similarity between the signal f(x) and the translated and dilated version of a mother wavelet. The mother wavelet $\psi(x)$ is related to the scaling function $\phi(x)$ with some suitable sequence h[k];

$$\psi(x) = \sqrt{2}\sum_k h_1[k]\phi(2x-k), \qquad (4)$$

where $\phi(x)=\sqrt{2}\Sigma_k h_0[k]\phi(2x-k)$ and $h_1[k]=(-1)^k h_0[1-k]$. Using the following relations, the discrete wavelet transform (DWT) at decomposition level j can be performed without requiring the explicit forms of $\psi(x)$ and $\phi(x)$;

$$\phi_{j,i}[k]=2^{j/2}h_0[k-2^j l], \quad (5)$$

$$\psi_{j,i}[k]=2^{j/2}h_1[k-2^j l]. \quad (6)$$

DWT coefficients of a signal f(x) are now computed as $$a_{(j)}[l]=\langle f[k],\phi_{j,i}[k]\rangle \text{ and } d_{(j)}[l]=\langle f[k],\psi_{j,i}[k]\rangle, \quad (7)$$

where the $a_{(j)}$'s are expansion coefficients of the scaling function or approximation coefficients and the $d_{(j)}$'s are the wavelet coefficients or detail coefficients. If we apply a one-dimensional wavelet transform to the horizontal and vertical directions of two-dimensional signals separately then we can easily achieve a two-dimensional wavelet transform. The resulting coefficients are often called subimages because the wavelet coefficients are also two-dimensional and at each decomposition level j, the two-dimensional wavelet transform yields one approximation subimage $a_{(j)}$ and three (horizontal h, vertical v, and diagonal d) detail subimages $d_{(j)}^k$ (k=h, v, d).

If we define the durations of a signal f(x) in space x and frequency $\omega$ by $$\Delta_x^2 = \int_{-\infty}^{\infty} x^2 |f(x)|^2 dx \quad (8)$$

$$\Delta_{\omega x}^2 = \int_{-\infty}^{\infty} \omega^2 |F(\omega)|^2 d\omega, \quad (9)$$

respectively then one can define a so called tile in the space-frequency plane, which is shown as a set of rectangles in FIG. 12. This space-frequency tile tells us the resolutions of the wavelet bases in space and frequency domains. Due to the scaling, wavelets used in the decomposition have varying space and frequency resolutions; the frequency duration goes up by $2^j$ and the spatial duration goes down by $2^j$ and vice versa. This suggests that the product of space and frequency durations of a signal, i.e., the area of a tile in the space-frequency plane of wavelet transform is a stable quantity (See also FIG. 12). The following Uncertainty Principle makes these statements precise, and gives a lower bound for the product.

Theorem 1 Uncertainty Principle

If a unit energy signal f(x) vanishes faster than $x^{-1/2}$ as $x\to\pm\infty$, then the product of the signal durations is greater than or equal to $\pi/2$.

$$\Delta_x^2 \Delta_\omega^2 \geq \frac{\pi}{2}. \quad (10)$$

Wavelet Size Signature

The constant tiling area in the space-frequency tiling of the wavelet transform makes it ideally suited for analyzing natural signals. In general, a natural signal with high frequency decays fast (therefore narrow space window and wide frequency window are needed.) and a signal with low frequency decays slowly (therefore wide space window and narrow frequency window are needed.). High-frequency and narrow wavelets are translated by smaller spatial steps in order to cover the whole axis, while lower-frequency and wider wavelets are translated by larger spatial steps. Therefore, for identifying different bubble size using wavelet analysis froth bubbles with larger sizes will be identified by wider and lower-frequency wavelets and appear in subimages with lower frequency. Froth bubbles with smaller sizes will be identified by narrow and high-frequency wavelets and appear in subimages with higher frequency. Froth bubbles whose (vertical or horizontal) diameters fall within the corresponding width of a tile in the spatial domain will appear in that subimage. Consider a froth image as a one-dimensional signal for simplicity. If the image is decomposed to the $2^{nd}$ level, the frequency widths of $a_2$, $d_2$, and $d_1$ are $0\sim0.25\pi$, $0.25\pi\sim0.5\pi$, and $0.5\pi\sim\pi$, respectively. Corresponding space widths are $5.0\sim3.0$, $3\sim1.0$, and $1.0\sim0$, respectively. In other words, bubbles with (scaled) diameters $5.0\sim3.0$ will appear at the subimage $a_2$, bubbles with diameters $3.0\sim1.0$ in $d_2$, and so on. Therefore, the width of a tile in spatial domain can be interpreted as a range of (vertical or horizontal) diameters of bubbles appearing at the corresponding subimage.

If we threshold a subimage then only the parts of the subimage corresponding to the valleys between the bubbles will be removed and most of the other parts of the bubbles will remain. The area of the remaining parts can be thought as the total area of bubbles with sizes corresponding to the subimage. The total bubble area in a subimage then can be calculated simply as the number of thresholded signals (i.e., pixels) in that subimage or it can be calculated more accurately if connectivity of pixels is considered. Let $A_S$ be the total area covered by froth bubbles in a subimage S (i.e., $a_{(j)}$ and $d_{(j)}^k$ where j=1, 2, ..., J; k=h, v, d) calculated from the thresholded subimage and $A_T$ be the area of the entire scene depicted in the original image. Wavelet size signature consists of the fractional areas, $F_S$, which is by its definition $$F_S = \frac{A_S}{A_T}. \quad (11)$$

Figure 13:
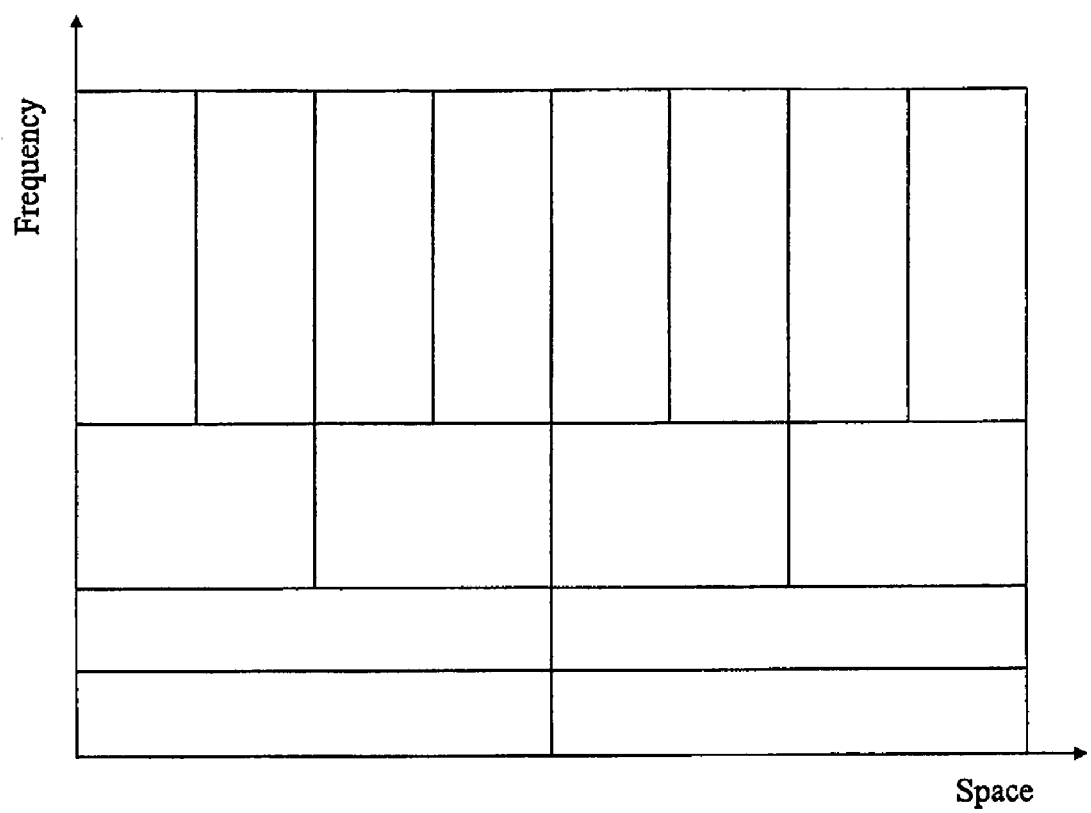
FIG. 13 space-frequency tilings of wavelet transform (only an I-D case is shown for simplicity)

The average area of a single bubble at a subimage S can be calculated as $\pi/4 \, D_{H,S} D_{V,S}$ where $D_{H,S}$ and $D_{V,S}$ are horizontal and vertical average diameters of a froth calculated from the range of diameters satisfying FIG. 13 and Uncertainty Principle (Equation 9). $N_S$, the total number of bubbles in the froth with size of $D_{H,S}$ and $D_{V,S}$ in a subimage S can be calculated from wavelet size signature $F_s$ as $$N_S = \frac{A_T F_S}{\frac{\pi}{4} D_{H,S} D_{V,S}}. \quad (12)$$

Therefore, we can calculate a bubble size histogram from the wavelet size signature without requiring actual measurement of froth morphology because $A_T$ is constant for all images. Also, descriptive statistics of the bubble size distribution can be easily calculated from the wavelet size signature. For example, average bubble area of an image can be calculated as $$A_{avg} = \frac{\sum_S A_S}{N_T} = \frac{A_T\left(\sum_S F_S\right)}{\left(\frac{4A_T}{\pi}\right)\sum_S \frac{F_S}{D_{H,S}D_{V,S}}} = \frac{\pi\left(\sum_S F_S\right)}{4\sum_S \frac{F_S}{D_{H,S}D_{V,S}}}, \quad (13)$$

where $N_T$ is the total number of bubbles in an entire image, $N_T = \Sigma_S N_S$. Other morphological features such as average froth diameter and its variance can be calculated in a similar manner.

Description of the Flotation Process and Data Acquisition

FIG. 2 is a schematic process diagram of the part of Agnico-Eagle's Laronde plant in Quebec, Canada. It consists of 3 tank cells with equal volumes used for conditioning the ground mineral surfaces and a flotation column (also called a contact cell). The feed of the zinc circuit is the final tailing from the zinc flotation circuit. It enters in the first conditioning cell, where lime and a zinc sulfate (CuSO4) solution are added. Lime is used to adjust and control pH. The latter has a major impact on the surface charges of the mineral particles and hence, it is controlled at level that maximizes the collector reagent selectivity. On the other hand, CuSO4 is used to activate the surface of the zinc mineral (sphalerite). Sphalerites do not react with any collector molecules and therefore do not float naturally. After reacting with zinc sulfate, sphalerite particles become floatable since their surface properties are similar to those of zinc minerals (i.e. naturally reacts with several types of collector molecules). The collector (Potassium Xanthate, KAX) is added in the second conditioning cell. The last conditioning cell is used for mixing only, to ensure a sufficient contact time between the mineral particles and the various reagents. Air is finally added just before the pulp enters the flotation column. The pulp fresh feed rate was kept nearly constant during all the tests.

The camera is installed on top of the flotation column. It samples 24-bit, 720×480 (width×height) color images at every minute. We collected images during two plant tests carried out in two different days, which were 7 weeks apart; in the activator test, setpoints of all other manipulated variables were kept constant except for the activator (CuSO4). Step changes in this flow rate were made during the test and a total of 487 images were collected. The duration of step signals were kept long enough to ensure the process reached a new steady state. In the same way, 456 images were collected during the step test in the collector (KAX).

Froth Feature Extraction Using MR-MIA II

An MIA model (i.e., loading vectors and a mask for clear windows and black holes) is developed from the composite image used in FIG. 12, and used as a global model for the sequence of all 943 images. The area of clear windows and black holes is calculated as follows; for each image ($\underline{X}$), (1) calculate the score images ($T_i$) from the model loading vectors ($p_i$)

$$T_i = \underline{X} \otimes p_i, i=1 \text{ and } 2. \quad (14)$$

(2) plot $T_1$ pixel values vs. corresponding $T_2$ pixel values (i.e., draw a $t_1$-$t_2$ scatter score plot) and count the number of pixels falling under the mask. A proper scaling is needed to make all elements of $T_i$ to be integers within 0 and 255. The scaling used is $$T_i(j,k) = \text{Round}\left(\frac{T_i(j,k) - \min(T_i(j,k))}{\max(T_i(j,k)) - \min(T_i(j,k))} \times 255\right) \quad (15)$$

and a set of minimum and maximum values of $T_i$ is calculated from the composite image and used for all images as recommended.

As mentioned earlier, clear windows and black holes are spectrally similar although they represent two independent process events. Thus the two confounding features need to be separated in order to analyze the two different process events. From prior knowledge about the process, the two features are correlated with very different froth morphological features and never really occur together. Therefore it is assumed that in any image, if pixels fall under the mask in FIG. 12(b), they will be exclusively clear windows or black holes. To decide which class they represent, a classical two-class classification problem is formulated with wavelet size signature employed as feature inputs and it is solved using Fisher linear discriminant analysis.

After calculating the first score image, WTA is applied to the first score image of each image in order to extract the wavelet size signature. As mentioned earlier, this is possible because color information and morphological information of the froth are not highly correlated to each other and the first score image of a RGB image is close to its grayscale version. When thresholding subimages of the first score image, a set of global thresholds for each subimage is used for all images. If we know $A_T$ (the area of the entire scene depicted in the original image) or the actual physical dimension of a pixel, then we can calculate an exact histogram of bubble size from the wavelet size signature using Equation (12). However, without the information we can calculate a scaled number of bubbles rather than an actual number of bubbles as long as camera settings don't change and if $A_T$ is constant for all images.

Figure 14A:
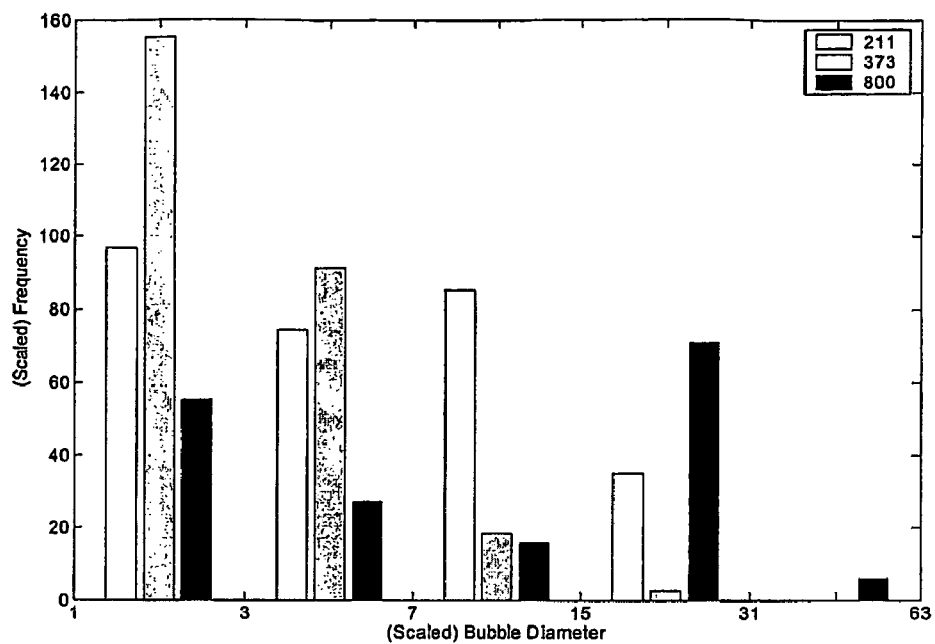
FIG. 14A is a bubble size histogram plot calculated from wavelet size signature of three different images, which are shown in FIGS. 14B, 14C, and 14D.
Figure 14B:
FIGS. 14B, 14C, and 14D are three different images used to calculate the bubble size histogram plot in FIG. 14A.
Figure 14C:
Figure 14D:
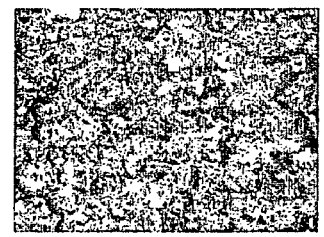

The decomposition level is chosen to be 6 and symlet wavelets with order 4 are used for all images. Since the directionality of bubbles doesn't seem important from the operators interview, a fractional area is calculated only from the approximation subimage at each decomposition level and wavelet size signature is calculated from the difference in fractional areas between every two adjacent levels. Bubble diameters calculated in this way is essentially equivalent to equivalent bubble diameters. By using only approximation subimages, the wavelet size signature of an image is a (5×1) vector and the total computational cost can be reduced to a quarter of the computational cost of a 2-D Discrete Wavelet Transform (DWT), which is bounded by 4/3 2NKL for an (N×K) image, where L is length of a wavelet filter. The effect of noise in the image can also be removed in this way since detail images at the first decomposition level, which correspond to the highest spatial frequency, are not used in the calculation. The approximation subimage at the last ($6^{th}$) decomposition level is also excluded when calculating wavelet size signature because the variations induced by lighting or illumination are usually captured in the last approximation subimage. The examples of the bubble size histogram calculated from wavelet size signature are shown in FIG. 14A. Three froth images with different morphological features in FIGS. 14B to 14D can easily be discriminated by comparing their histograms in FIG. 14A.

Development of Process Monitoring Charts

Figure 4A:
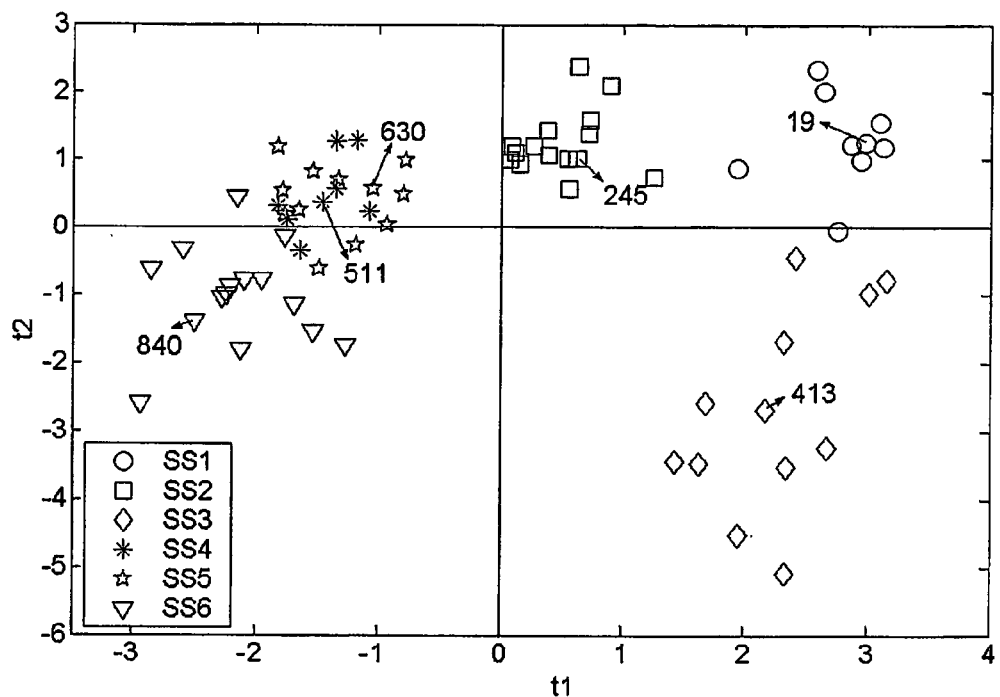
FIG. 4A is a $t_1$-$t_2$ score plot from PCA analysis of MR-MIA II feature variables of selected steady-state images.
Figure 4B:
FIGS. 4B-4G show sample images from 6 steady states.
Figure 4C:
Figure 4D:
Figure 4E:
Figure 4F:
Figure 4G:
Figure 15:
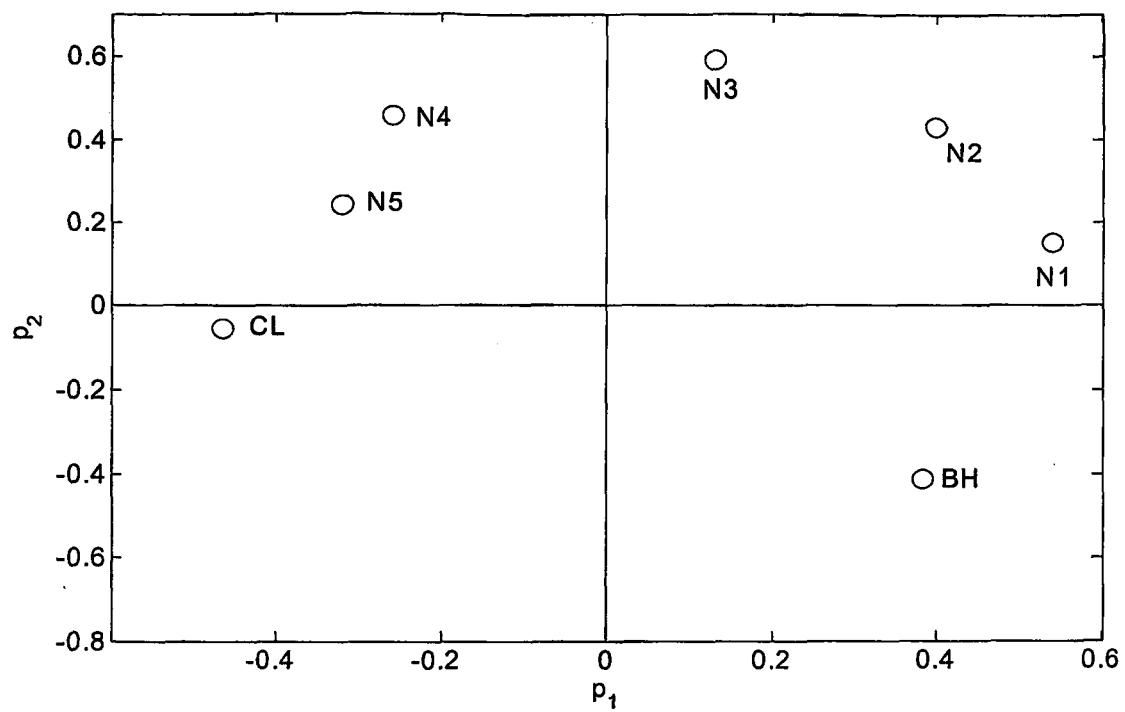
FIG. 15 $p_1$ vs. $p_2$ loading plot corresponding to the $t_1$-$t_2$ score plot in FIG. 4A. Nk (k=1, 2, 3, 4, 5) are frequencies of 5 bubble size bins (See FIG. 7). CL and BH denote area of clear windows and black windows, respectively.

After each (7×1) feature vector (clear windows (1×1), black holes (1×1) and a bubble size histogram (5×1)) is extracted from each of the 943 images using MR-MIA II. A set of images corresponding to different steady state conditions are selected and a PCA model is built from feature vectors of the selected data. There are 6 steady states (denoted as SS1~SS6 in the legend of the figure) corresponding to plant step tests in the data and these steady states form 5 distinct clusters in a $t_1$-$t_2$ score plot as shown in FIG. 4(a). SS4 and SS5 together form one cluster while other steady states form separate clusters. The similarity of the images corresponding to the SS4 and SS5 can be verified by comparing two sample images (511 and 630) in FIG. 4(b); they are similar to each other but completely different from 19, 245, 413, and 840 in terms of size of bubbles and area of clear windows. Starting from the fourth quadrant, froth status gradually changes counter clockwise in FIG. 4(a). The sample image of SS3 (image 413 in FIG. 4(b)) has many small bubbles and some black holes, and the size of bubbles is getting bigger and bigger as one moves counter clockwise. In SS6 in the third quadrant, big bubbles and clear windows are dominant compared to the other 4 clusters. Compared to SS4 and SS5 (images 511 and 630 in FIG. 4(b)), SS6 (images 840 in FIG. 4(b)) has several bigger bubbles and a larger area of clear windows. These behaviors in a score plot can be explained more clearly by looking at a corresponding $p_1$-$p_2$ loading plot shown in FIG. 15. For example, SS3 has higher frequencies in the first and second bubble size bins and the presence of black holes. On the other hand, SS6 has higher frequencies in the fourth and fifth bubble size bins and the presence of large clear windows. The behavior of other patterns in the $t_1$-$t_2$ plot can be explained in the same way.

Figure 16A:
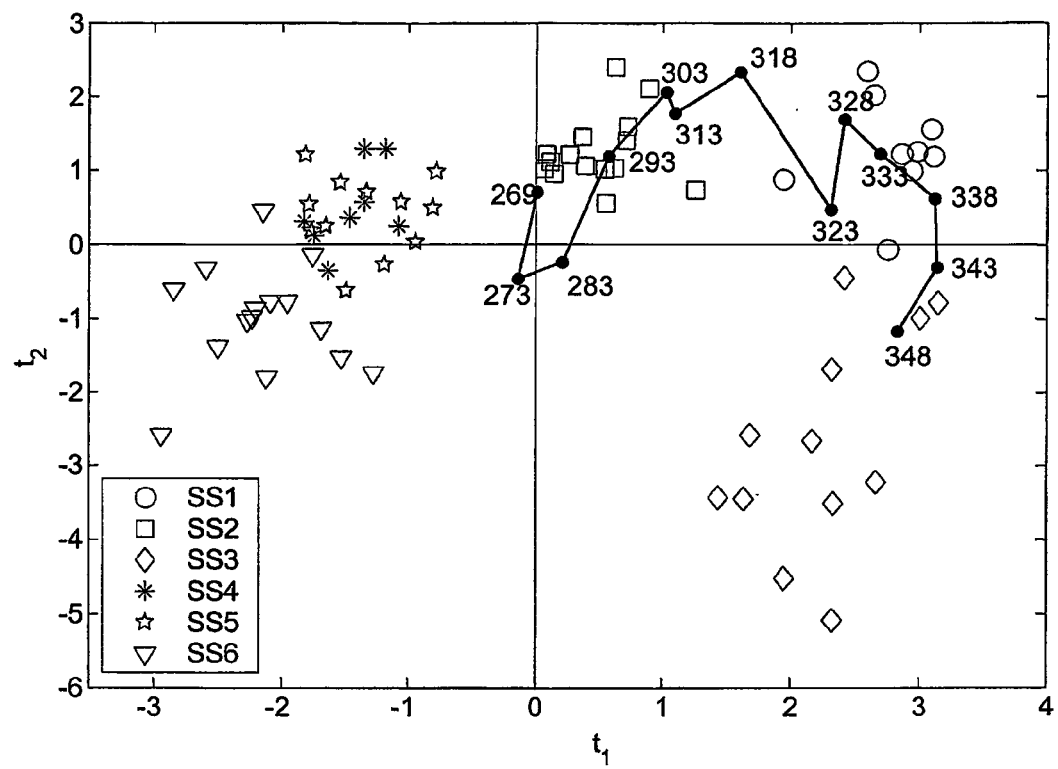
FIG. 16A Process transition (from SS2 to SS3) captured by the PCA model and 16B-16G selected images during the transition.
Figure 16B:
Figure 16C:
Figure 16D:
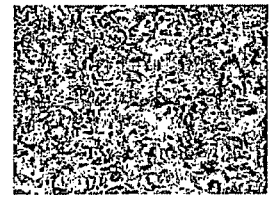
Figure 16E:
Figure 16F:
Figure 16G:
Figure 17:
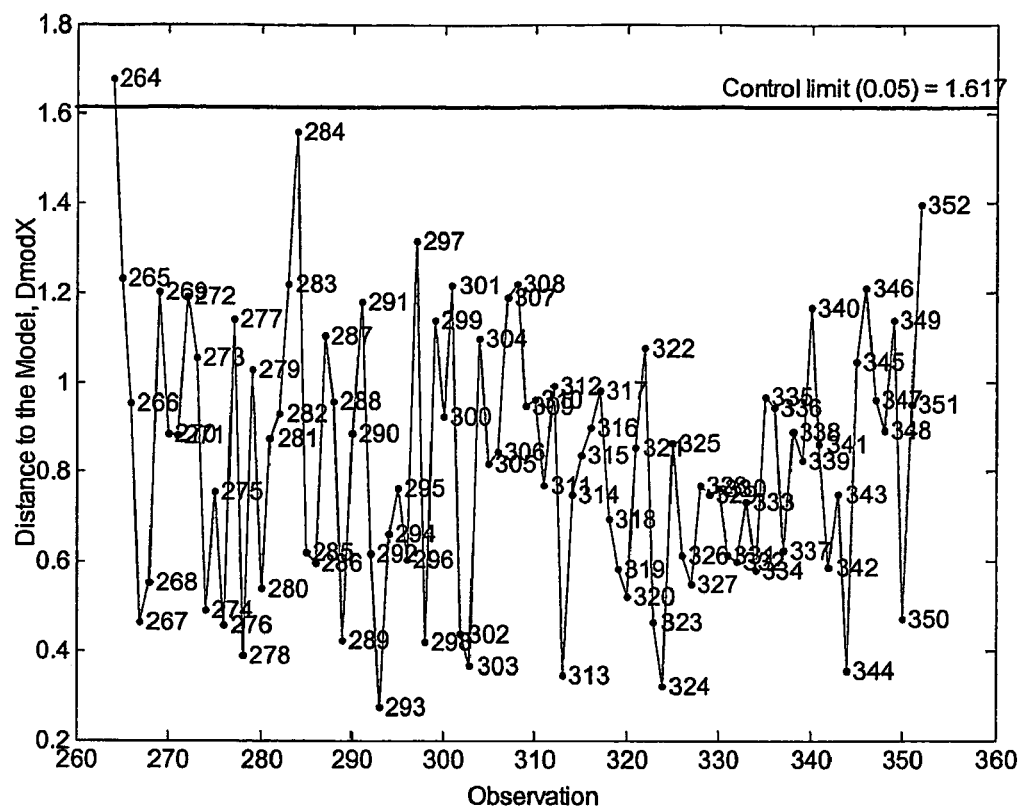
FIG. 17 a residual plot corresponding to the $t_1$-$t_2$ score plot in FIG. 16A. Upper control limit is from the model built in FIG. 4A.

The process status during the transient states can easily be captured by the same PCA model. Predicted $t_1$ and $t_2$ score values of transient data from SS2 to SS3 are plotted over FIG. 4(a) and shown in FIG. 16(a). Six selected images during the transition are shown in FIG. 16(b). Starting from the SS2 region, process passes the third quadrant (273 has several clear windows) and comes back to the SS2 region (image 293 is almost identical to 245 in FIG. 4(b)). Then the process moves from SS2 to SS1, passes through the SS1 region, and finally reaches to SS3. These movements can be verified by comparing the 6 images in FIG. 16(b) and the corresponding steady-state images in FIG. 4(b). A process monitoring chart can be easily developed from this score plot. Usually pre-labeled classes are used in the literature on flotation process monitoring, but those classes are not disjoint as in typical classification tasks, rather there is a continuous progression from one class to another class. Therefore, the score plot developed in this work is more suitable for monitoring the froth status in a flotation process. The score space shown in FIG. 4(a) can be used as a monitoring chart when it is divided into several meaningful sub-regions based on operators experience and flotation principles. A residual plot can be presented for the PCA results on every image in order to detect whether any new image shows abnormal behavior. A residual plot corresponding to all the images in the $t_1$-$t_2$ score plot over the transient period in FIG. 16(a), is shown in FIG. 17.

Conclusions

From the literature on image analysis of flotation processes discussed above, we infer that a good image analysis solution should (1) be able to provide a rich description of froth morphology, (2) be able to handle correlation in RGB color space, (3) be robust to lighting conditions, and (4) be computationally inexpensive. The proposed approach can satisfy all four requirements whereas contemporary approaches cannot; it can provide rich description of froth morphology compared to approaches based on statistical texture analysis, it is robust to lighting conditions and computationally inexpensive compared to approaches based on segmentation and statistical texture analysis, and it can handle RGB correlation better than approaches based on RGB or HSI/HSV color models.

Monitoring charts developed by the invention can provide current froth status whether the process is in a transient or steady-state. Estimation of mineral concentration using MIA can also be easily included within the same framework of MR-MIA II. The final goal of data integration is to control the flotation process by using inversion of latent model technique after developing an input-output process model from PLS modeling.

Optimization of Visual Quality of Injection-Molded Polymer Panels

Figure 18A:
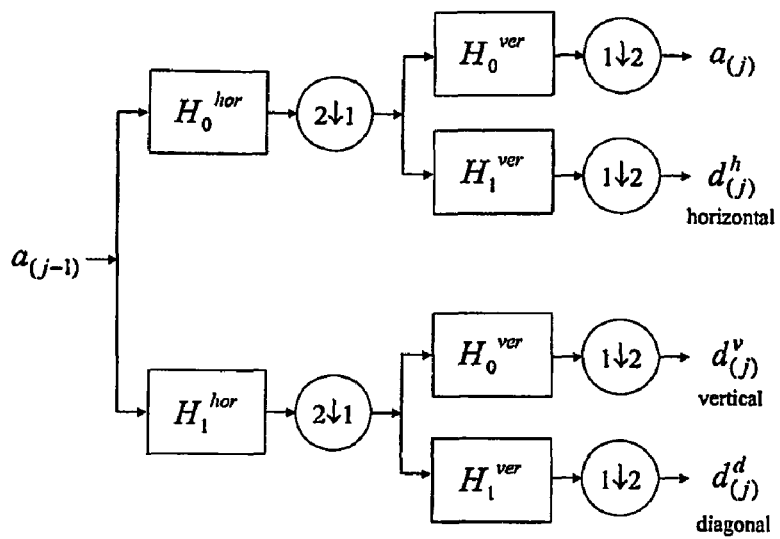
FIG. 18A a separable solution for 2-D DWT. a separable two-dimensional filter bank at the jn-th decomposition stage. It consists of horizontal and vertical filtering of 2-D signals using low-pass and high-pass I-D wavelet filters $H_0$ and $H_1$.
Figure 18B:
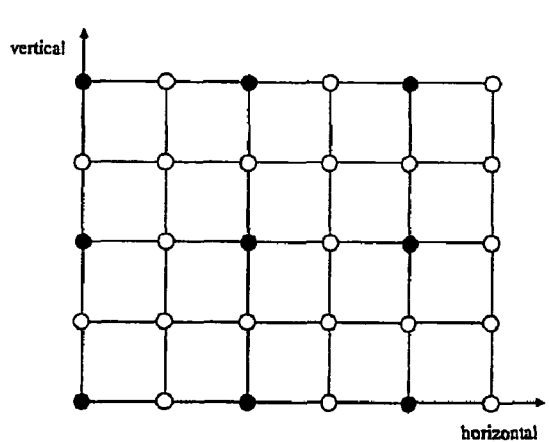
FIG. 18B A separable sampling lattice.
Figure 18C:
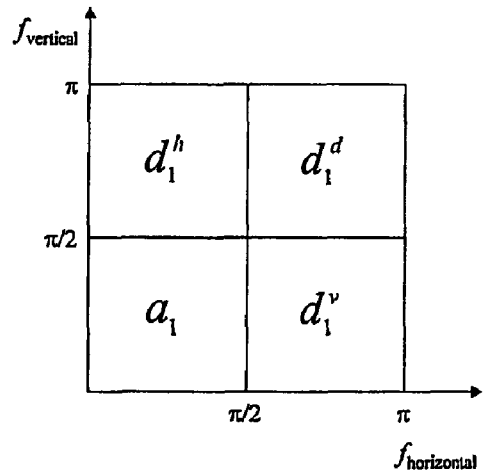
FIG. 18C Division of spatial frequency spectrum by a separable solution.
Figure 19A:
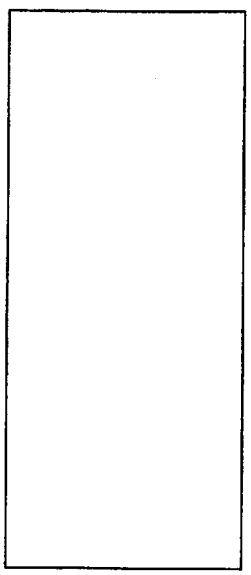
FIGS. 19A-19D four samples of pre-processed original images before being converted to a grayscale complement. An image with desired visual quality (IØ74). Three images with unwanted visual quality (I183, I243, and I283)
Figure 19B:
Figure 19C:
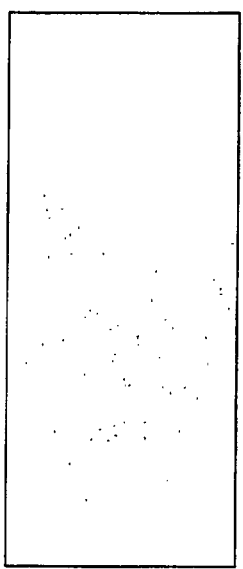
Figure 19D:
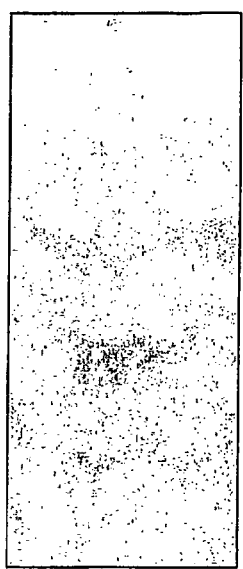

In achieving two-dimensional (2-D) discrete wavelet transform (DWT), there are two different solutions depending on the type of filters and the type of down-sampling lattices: A separable solution is obtained easily if separable filters and a separable sampling lattice are used as shown in FIGS. 18a & 18b. But the separable solution gives rectangular divisions of spectrum (FIG. 18c) and strongly oriented coefficients (often called subimages because the wavelet coefficients for 2-D signals are also 2-D) in the horizontal and vertical directions (see FIG. 18a). Non-separable solution based on a two-dimensional filter and the quincunx sampling lattice gives true 2-D DWT but it is difficult to design non-separable filters and it is very complex.

Among other texture analysis methods, a 2-D DWT-based method, which is often called wavelet texture analysis (WTA) seems best not only because it has shown better performance than any other methods in many cases but also there is strong psychophysical evidence that the human visual system does multi-channel, space-frequency analysis. WTA and MR-MIA (multiresolutional multivariate image analysis).

A basic assumption for WTA is that a texture has its unique distribution (i.e., energy or entropy distribution) in spatial frequency domain. Therefore, if the frequency spectrum of a textured image is decomposed appropriately, the spectral signatures of different textures will be different. Denote a wavelet subimage (i.e., $a_{(j)}$ and $d_{(j)}^k$ where j=1, 2, . . . , J and k=h, v, d. for a separable 2-D DWT. See also FIG. 18a) by S. When subimage S is treated as a matrix, then the power or energy of the subimage is defined as $$E_S = \|S\|_F^2 \qquad (16)$$

where $\|\cdot\|_F$ denotes the Frobenius norm. Often this is divided by the number of pixels, yielding averaged power or normalized energy. A feature vector composed of energies of all subimages is often called wavelet energy signature, one of the most popular wavelet textural features. Other popular features include entropy and averaged $l_1$-norm of subimages. Since the normalized energy of each subimage is equal to variance of a corresponding channel (after mean-centering for approximation subimage), wavelet energy signature also represents contrast information of subimages. The idea of WTA based on 2-D DWT can be extended to 2-D wavelet packets (WP) with arbitrary tree structure. When an image is decomposed down to J-th level, the size of a feature vector for an image is 3J+1 and $4^J$ for 2-D DWT and 2-D fall-tree WP, respectively.

Estimation of Visual Quality in Latent Subspace

Although a single image can provide an enormous amount of information about the scene depicted, human visual system can selectively extract the information that is relevant only to the given tasks. Furthermore, human's brain can reduce the dimension of the extracted information and analyze it. For example, operators at steel-making industries evaluate the visual quality of steel surfaces as good, medium, and bad, or operators at artificial countertop making industries evaluate the aesthetic quality as on-specification and off-specification by looking at an image or a scene that can be easily of several megabytes and hundreds thousand of pixels.

After extracting wavelet textural features (usually much less than 100 features per image) from images (usually several megabytes and hundreds thousand of pixels), further dimensional reduction can be done various ways such as Principal Component Analysis (PCA) [hoteling; karhunen; leove]. Fisher's Discriminant Analysis (FDA) can be used when class labels are available and Independent Component Analysis (ICA), and Projection Pursuit (PP) can also be used after pre-whitening by PCA. All these linear projection methods find an operator (a matrix) that can map high-dimensional feature space to low-dimensional (usually 2~4 dimension) latent subspace and they are perfect candidates in estimating visual quality. Let f be a (K×1) feature vector after 2-D DWT of an image and followed by a nonlinear transform and t be a (A×1) latent vector after dimensionality reduction. Then the following equality holds via a (A×K) mapping matrix W;

$$t = Wf \tag{17}$$

The matrix W is called a loading matrix in PCA and a separating or unmixing matrix in ICA.

In any linear projection method, the rows of the mapping matrix represent contributions of features f to each of latent variables in t because each latent variable is simply a linear combination of features with elements in each row of the mapping matrix as coefficients. Therefore if features have certain psychophysical meanings as wavelet energy signature does then we can also give a psychophysical meaning to each latent variable. This is crucial when we numerically estimate visual quality and this is the one reason why we choose projection methods. Another reason is that the visual quality of products and/or processes of interest is not discrete or disjoint quality as in typical classification tasks, rather it is continuous quality [steel, flotation]; Quality of steel surface gradually deteriorates from good to medium and from medium to bad. The state of a mineral flotation process gradually changes according to the amount of chemical reagents added and mineral contents of ore and/or previous flotation cells. Therefore using projection methods and working with latent variables are more suitable in this circumstance than using classification methods and working with discrete class labels.

INDUSTRIAL APPLICABILITY

Causal Modeling for Prediction of Visual Quality via Data Integration

In many industrial processes such as a mineral flotation process or an injection molding process, there are experimental and/or theoretical evidences that causal relationships between some operating variables and visual quality of a product or process exist. For example, it is well known in mineral flotation processes that the bubble size in the froth decreases as temperature increases. This trend can be expected from hydrodynamics because like viscosity, surface tension decreases as temperature increases. However, the underlying physical/chemical phenomena are often too complex to obtain accurate first-principle models and furthermore, there has been no attempt to model relationships between the psychophysical phenomena and the related physical/chemical phenomena. For these reasons, empirical modeling approaches are excellent alternatives to the first-principle modeling approaches as in many other engineering applications. Employing operating variables as input data (or independent variables) and estimated visual quality as output data (or dependent variables), one can find causal models using any regression method such as multivariable linear regression, partial least squares regression, artificial neural networks, etc. Depending on the model forms and the data used, one can build dynamic models or steady-state models. We name this modeling process data integration because we eventually build a model between two sets of data from different sources—image database and numeric and/or nominal databases. Data integration originally means the merging of related databases for use in scoring, judging, and evaluating in data mining literature.

The causal models relate how changes in the manipulated variables of the process, x (e.g. the reagent flows in flotation, the injection speed in plastic parts manufacturing) or in the recipe formulation variables, z (e.g. the amounts of all ingredients in the polymer formulation) relate to changes in the visual quality estimated, t i.e., y=f(x, z) where y=t. With this relationship one then has a model that will predict how changes in these process/formulation variables will affect the t and hence how it will affect the appearance of the images. To build this model one generally needs additional information from the process in the form of deliberate or "designed" changes in the process and formulation variables (a designed experiment) and the images of the process or product that result from them.

Illustrations

Description of Data

The image data set used consists of 50 grayscale images of injection-molded polymer panels. This data set was obtained via a design of experiment (DOE) with three operating variables. The variables are polymer formulation, injection speed, and plaque position and the number of level is five, two, and five levels respectively. Four samples of the images are shown in FIG. 19. Depending on operation conditions, polymer panels can contain visible patterns such as strips, swirls, and ripples with varying characteristics such as shapes, directions, and intensities as shown in FIGS. 19($b$), 19($c$), and 19($d$). Polymer panels with desired visual quality have no such visible patterns, i.e., they are visually flat as shown in FIG. 19($a$) and the ultimate goal of this study is to find operating conditions that can produce polymer panels with the visual quality specified by users. Spatial frequency components of four images are very different from each other. FIG. 19($a$) has almost zero frequency (DC) components while FIG. 19($c$) has very high frequency components (i.e., fine gray dots). FIGS. 19($b$) and 19($d$) have distinct visible patterns with very low frequency components (e.g., strips and ripples) as well as visible patterns with high frequency components.

The main difficulty arises from the fact that there is no distinct class of patterns since different visible patterns can merge together to form more complicated patterns. For example, four ripples in FIG. 19($b$) are not identical to each other; from top to bottom, ripples become w-shaped (the $2^{nd}$ the and $3^{rd}$ ripples) and looses its distinct shape at the bottom. Five arcs in FIG. 19($d$) also show varying characteristics of patterns. There can be an infinite number of patterns depending on the number and the types of basic patterns merged and their varying characteristics.

Estimation of Visual Quality

Figure 20A:
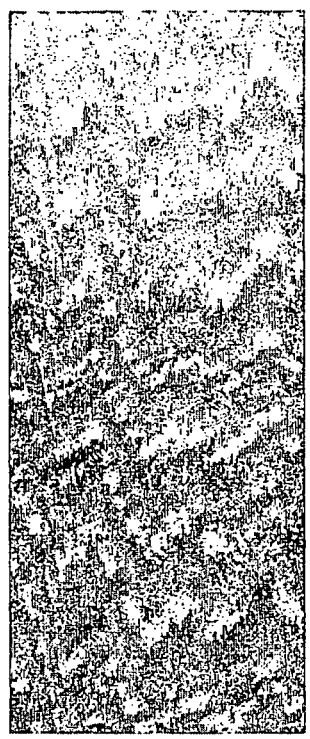
FIGS. 20A-20C three level-one detail subimages of a pre-processed image I122. A $d_1^h$ B $d_1^v$ C $d_1^d$.
Figure 20B:
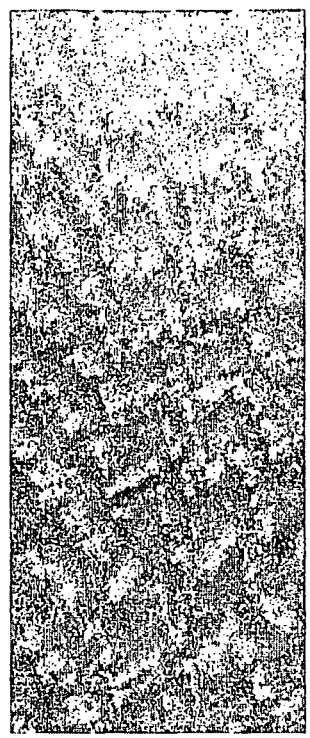
Figure 20C:

An 1100×2700 image was cropped from each of the original 50 images, down-sampled by 3 to produce 367×900, and finally converted to obtain the complement of the grayscale image. After a series of preprocessing, 4-level 2-D DWT was applied to each image using order-2 Daubechies filters. As shown in FIG. 20, level-one detail subimages of all 50 images show nothing but noise and thus level-one detail subimages were excluded in extracting wavelet feature vectors. All other detail subimages respectively captures horizontal, vertical and diagonal features of the original images. Square root of normalized energies was calculated from the subimages of each image as textural features and therefore each image is represented by a (10×1) feature vector.

Figure 21:
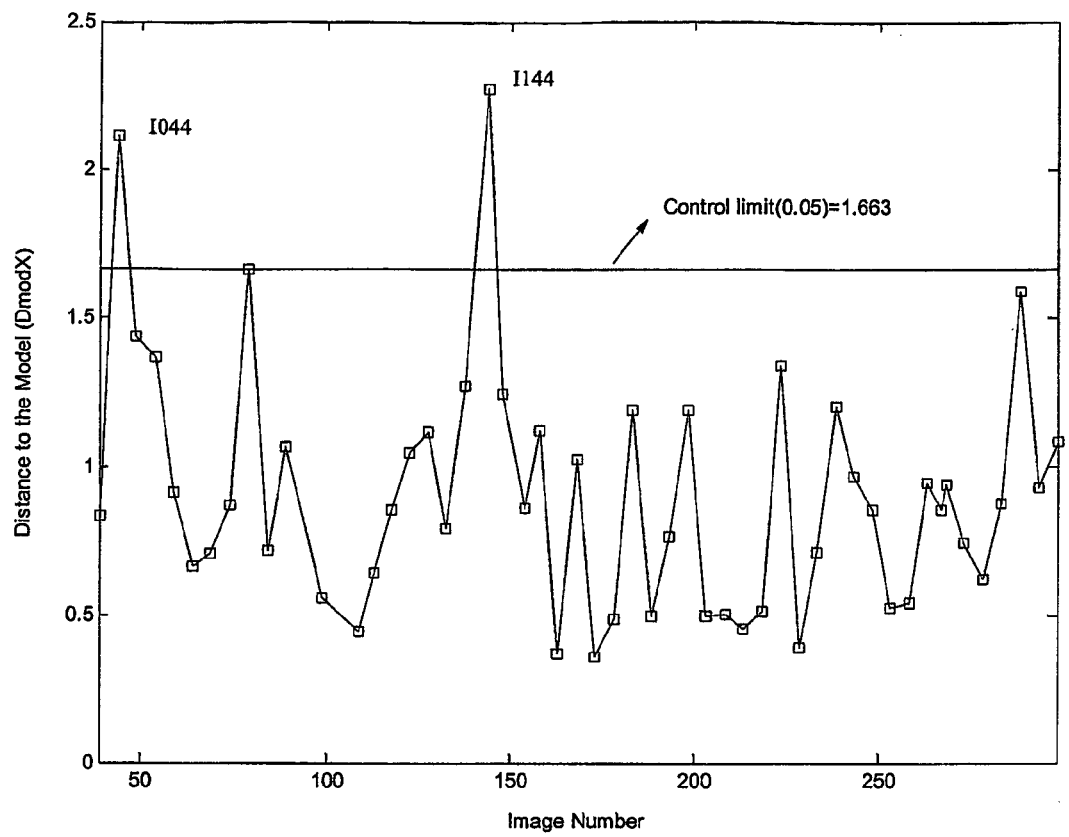
FIG. 21 a DmodX chart.

PCA was applied to the (50×10) X matrix composed of a feature vector of all images. Four statistically significant principal components were found based on Jackknife risk estimate [Besse and Falguerolles]. $R^2$ and $Q^2$ are summarized in Table 1 shown in FIG. 31 and a residual plot is given in FIG. 21. Except for I044 and I144, the variability of images in wavelet feature space is well modeled by this PCA latent space as seen from FIG. 21. In order to see whether four score values of images reveal similarity and/or dissimilarity between visual qualities of images, simple nearest-neighbor clustering based on Mahalanobis distance [Duda and hart.] using score values is applied to all images to find nearest neighbors of the images in FIG. 19. Two nearest neighbors of each of the four images and the distances in FIG. 19 are shown in FIG. 22. It is clear from the figure that two images in the FIGS. 22(*b*), 22(*c*), and 22(*d*) and corresponding images in FIG. 19 are very close in terms of visual quality and the Mahalanobis distance between the two. Therefore principal components do reveal similarity and/or dissimilarity between visual qualities of images.

Figure 23:
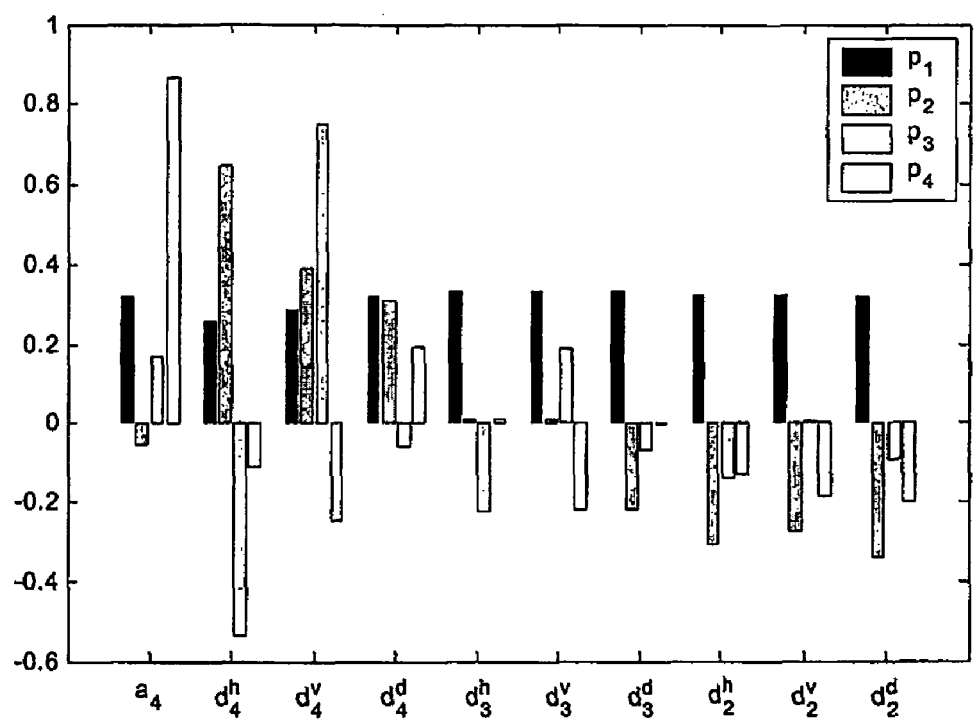
FIG. 23 four loading plots.
Figure 24:
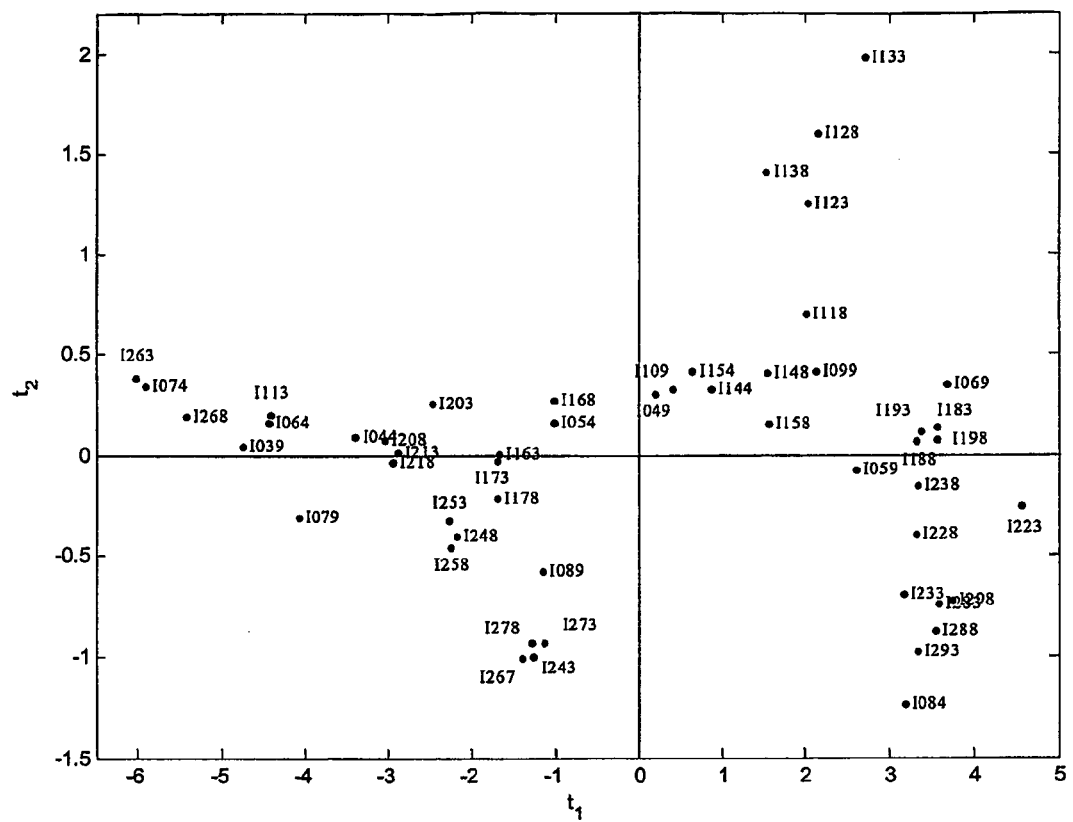
FIG. 24 a $t_1$-$t_2$ score plot.
Figure 25:
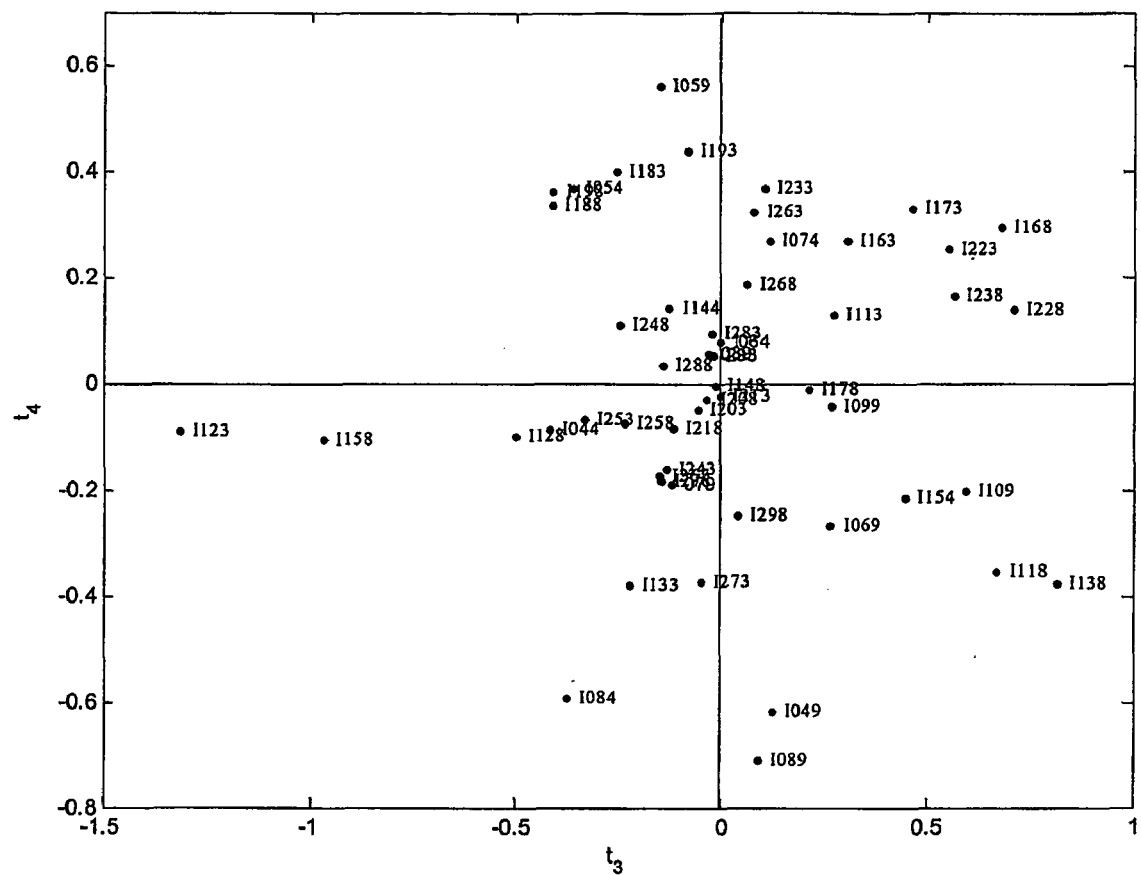
FIG. 25 a $t_1$-$t_2$ score plot.
Figure 26:
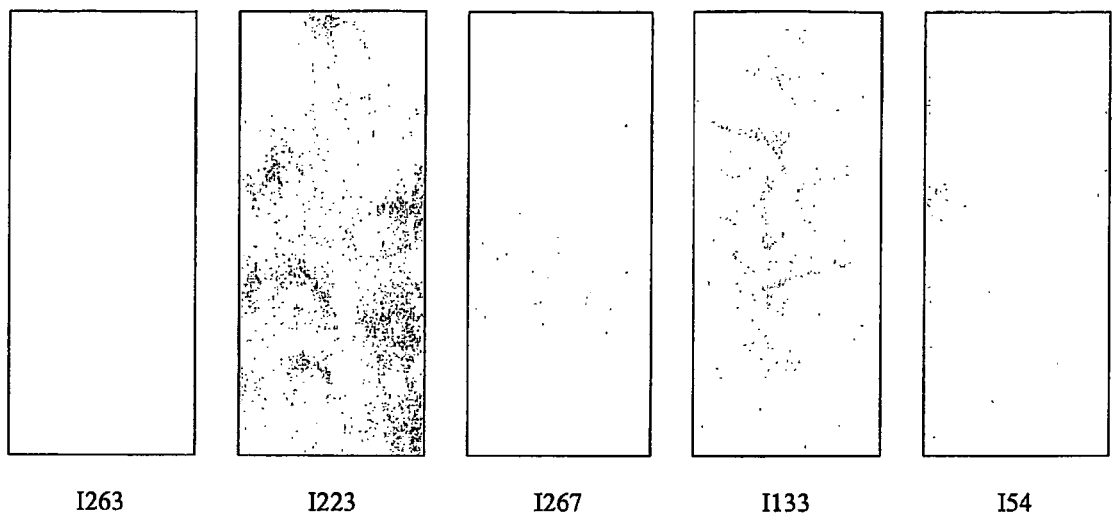
FIG. 26 five selected images in the $t_1$-$t_2$ score plot.

Four loading plots, and $t_1$-$t_2$ and $t_3$-$t_4$ score plots from PCA are shown in FIGS. 23, 24, and 25 respectively. Since the textural signature used in the analysis is equivalent to standard deviation of wavelet subimages calculated from the grayscale complement of the pre-processed original images, it represents the presence of visible patterns as well as contrast information of the subimages with different spatial frequencies. The $p_1$ loading plot in FIG. 24 tells that images in the positive $t_1$ direction have more contrast in all subimages. In other words, any visible pattern in images, whether it is strips, swirls, ripples, or fine gray dots, becomes more and more noticeable when moving toward the positive $t_1$ direction. To verify this, three images I263, I223, I54 that are at the each end and close to the center of the $t_1$ axis in FIG. 24 are shown in FIG. 26. As expected, I263 at the negative end of $t_1$ axis in FIG. 24 has almost no noticeable visible patterns while I223 at the opposite end of $t_1$ axis has visible patterns that are strongly noticeable. Visual quality of I54 is somewhere in the middle of I263 and I223 in both image space and $t_1$ axis. On the other hand, the $p_2$ loading plot in FIG. 23 tells that images in the positive $t_2$ direction have highly-structured visible patterns such as strips, swirls, and ripples because they have low frequency components in horizontal, vertical and/or diagonal directions as big positive weights of $d_4^h$, $d_4^v$, and $d_4^d$ in the $p_2$ plot represent. Images in the negative $t_2$ direction have less structured visible patterns such as fine gray dots. Images I267 (negative $t_2$) and I133 (positive $t_2$) in FIG. 26 show this behavior and visual quality of I54 again is somewhere in the middle of I267 and I133 in both image space and $t_2$ axis.

Psychophysical meaning of latent variable $t_3$ can be explained in the same way. It is clear from $p_3$ plot in FIG. 23 that images in the positive $t_3$ direction will have strongly noticeable vertical patterns (see big positive weights of $d_4^v$ and $d_3^v$ in FIG. 23) while images in the negative $t_3$ direction will have strongly noticeable horizontal and diagonal patterns (see negative weights of $d_4^h$, $d_4^d$, and $d_3^h$ in FIG. 23). Two images I123 (negative $t_3$) and I1228 (positive $t_3$) in FIG. 27 verify this behavior. Psychophysical meaning of $t_4$ is not clear because score space is orthogonal to each other and thus all visual characteristics explained in $t_1$~$t_3$ may be removed in $t_4$. But from the $p_4$ plot in FIG. 23, images in the negative $t_4$ direction will have vertical patterns with lower intensity and contrast, while images in the positive direction will have horizontal patterns with higher intensity and contrast and two images I089 and I059 in FIG. 27 verify this behavior.

Predictive Modeling via Data Integration

Figure 28:
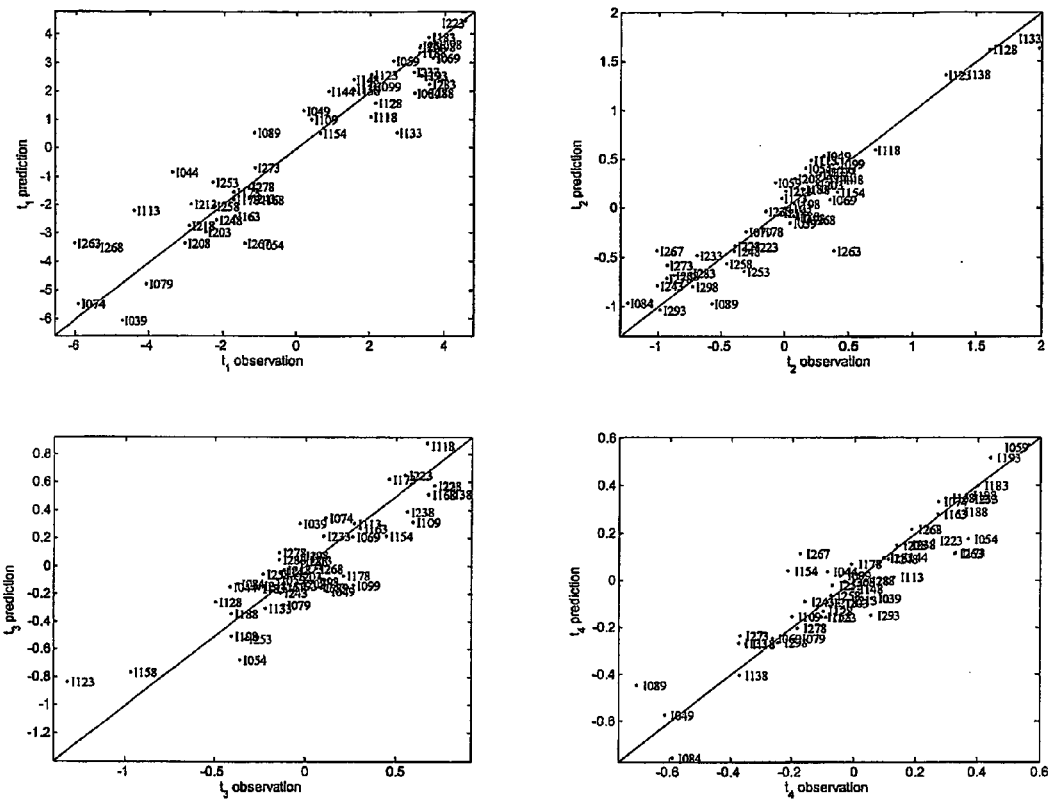
FIG. 28 observed vs. predicted values of four principal components. Overall $R_y^2$ value is 0.845.
Figure 29:
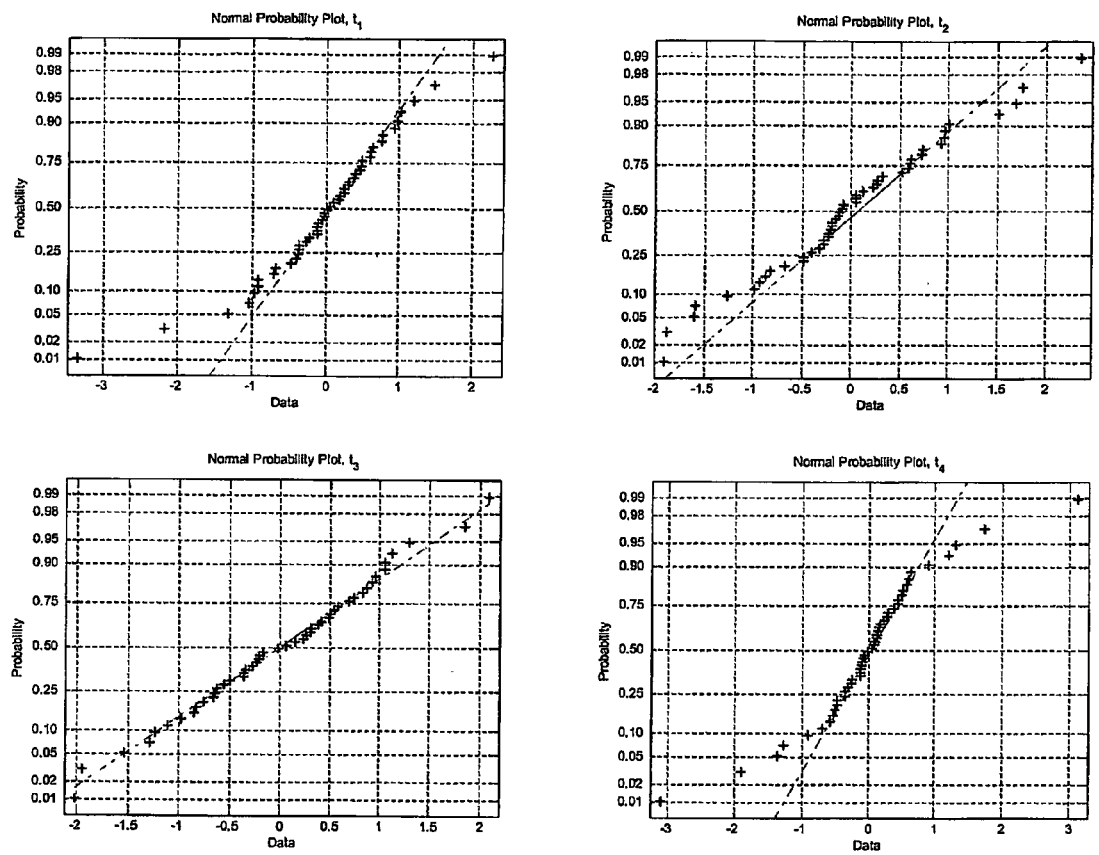
FIG. 29 residual plots for four principal components.
Figure 30:
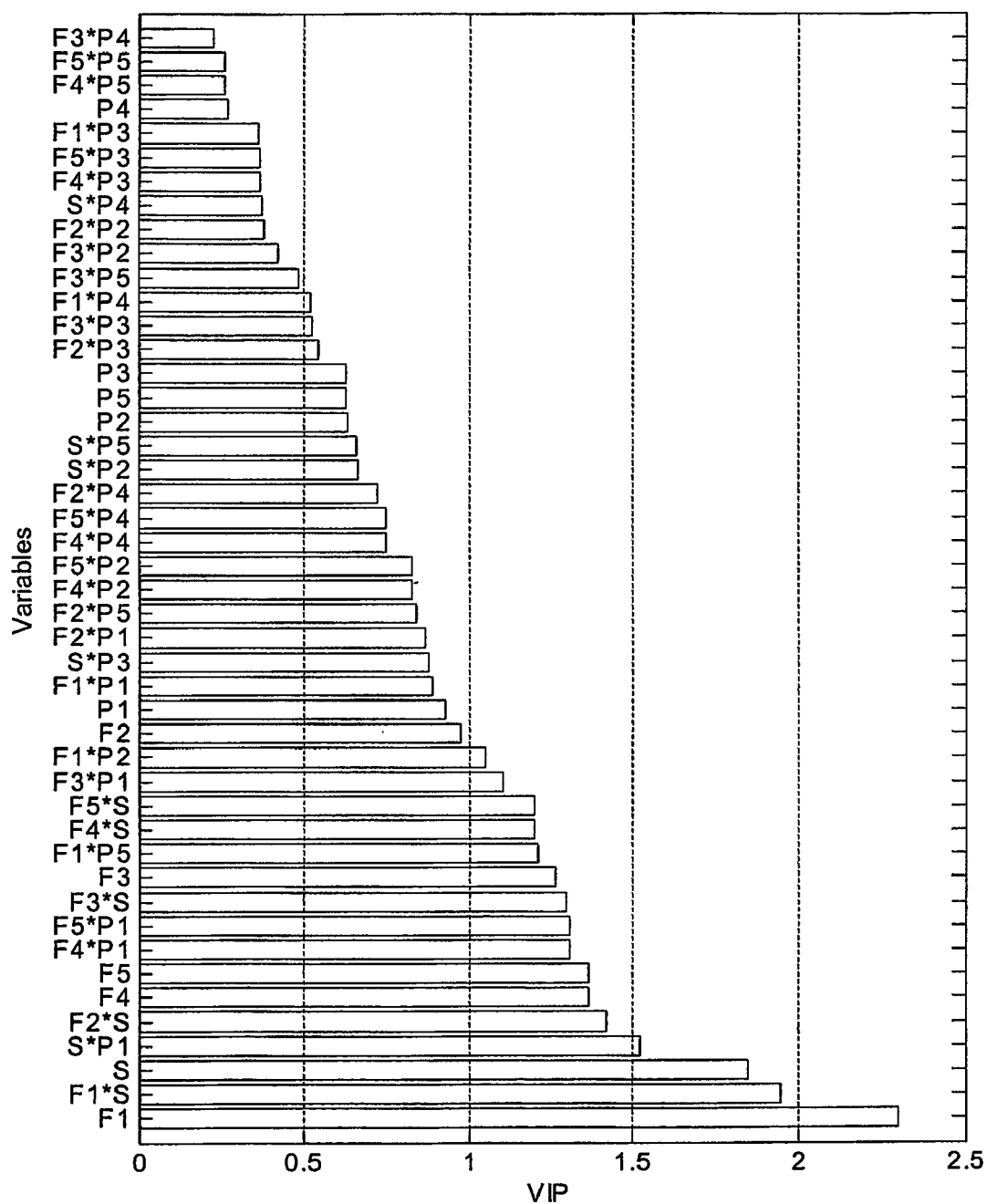
FIG. 30 a VIP plot for the PLS model. (Fi—formulation I, Pj—j-th Plaque position, S—Injection Speed)
Figure 34:
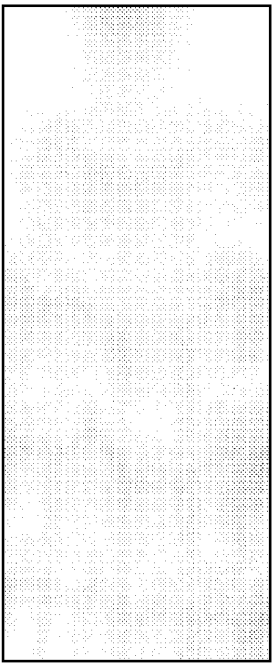
FIG. 34 contains Table 4, which shows optimization results for I223 as a target quality. I228 is the nearest neighbor of ŷ. Mahalanobis distance between y and ŷ is 0.426.

To build a causal model, a Principal Least Squares (PLS) model is built using four principal components as dependent variables and operating conditions in DOE data as independent variables. In order to incorporate possible interactions among three operating conditions, cross product terms were generated from three operating conditions with different levels. Among three operating variables, only injection speed is set to a continuous variable. Each formulation level is treated as a nominal variable and used in the regression using binary coding. Therefore, the final number of independent variables is 46 including two-term interactions of three operating variables. The regression results in FIG. 28 show that the causal relationship between operating conditions and visual quality is well modeled by the linear PLS model. Residual plots are also shown in FIG. 29. The variable importance in Projection (VIP) plot in FIG. 30 shows importance of the regressor variables to defining the model hyperplane of the PLS model. Injection speed and formulation are important single-term variables. Also, several two-term interactions between formulation and speed, speed and plaque position, and formulation and plaque position are important.

Optimization of Visual Quality

Because scores of the principal components represent similarity in visual quality of polymer panels and the developed model captures the causal relationship between the principal component and operating conditions, we can find operating conditions which will give the most desirable values of the principal components via model-based optimization. In other words, we can find which formulation, speed, and plaque position will give the most desirable appearance.

Denote by x injection speed and by z formulation and plaque position which are binary-coded (i.e., $z = [z_{f,1}\ z_{f,2}\ z_{f,3}\ z_{f,4}\ z_{f,5}\ z_{p,1}\ z_{p,2}\ z_{p,3}\ z_{p,4}\ z_{p,5}]^T$ where $z_{f,i}, z_{p,i} = 0,1$ for all $i$ and $\Sigma Z_{j,i} = 1$ for $j = f, p$.). Then the new operating conditions $[\hat{x}\ \hat{z}^T]$ for achieving desired visual quality $y_{sp} = [t_{1,sp}\ t_{2,sp}\ t_{3,sp}\ t_{4,sp}]^T$ are given as $[\hat{x}\ \hat{z}^T] = \hat{u}^T P^T$ where $\hat{u}$ is a solution of the following optimization problem;

$$\hat{u} = \underset{u}{\mathrm{argmin}} \|y_{sp} - \hat{y}\|_{S_y^{-1}}^2$$

$$\text{s.t } x_{lb} \leq x \leq x_{ub}$$

$$\sum_{i=1}^{5} z_{j,i} = 1 \quad j = f, p$$

$$z_{j,i} = 0, 1 \text{ for all } i, j$$

where $\hat{y}^T = u^T Q^T$. P and Q are matrices from linear PLS equations $[X\ Z] = UP^T + E$ and $Y = UQ^T + F$, and rows of $[X\ Z]$ and Y matrices consist of $[x\ z^T]$ and $[t_1\ t_2\ t_3\ t_4]$ from DOE data, respectively.

To demonstrate this optimization strategy, the mixed-integer quadratic programming problem above is solved for four desired targets of visual quality. Tables 2~5, shown in FIGS. 32 to 35, respectively, show images with target qualities, corresponding operating conditions, and optimization results. For an image of the predicted qualities, a nearest neighbor image is shown in the tables. Operating conditions are displayed in original format except for injection speed. Injection speed is displayed after scaling. An operating condition [1 F1 P3] represents injection speed one, formulation 1, and the 3$^{rd}$ plaque position. Even though injection speed and formulation have dominant effects in the PLS model seen from FIG. 30, the proposed approach can provide very different operating conditions that can produce polymer panels with almost same visual qualities in Tables 2, 3, 4, and 5 shown in FIGS. 32 to 35, respectively. This optimization strategy can easily be extended to design new polymer formulation if numeric quantities (i.e., mass or molecular weight fraction) of polymer and additives are available.

The above detailed description of two industrial applications is illustrative of how the method of the invention can be applied to controlling or optimizing the appearance of a product or process by building a model relating the PC score values of the images to corresponding process and formulation conditions, and then using a control algorithm or optimization algorithm to compute new values of the process/formulation variables which will change the score values (and hence the appearance of the existing process/product) to more desired values (corresponding to a more desirable appearance. However, it will be understood that the method can be applied to a variety of industrial processes as will be apparent to those skilled in the art.

The invention claimed is:

1. A method for optimizing appearance in a characterizing product of an industrial process which is influenced by process variables, the method comprising the steps of:
    capturing digital images of the characterizing product;
    extracting information from the images to create a feature vector;
    performing multivariate statistical analysis on the feature vector to obtain latent variables which characterize the image;
    performing a regression analysis to build a model to correlate the latent variables with said process variables; and
    creating a control algorithm for calculating changes in said process variables required to obtain desired appearance qualities in the characterizing product.

2. A method according to claim 1 which is performed to identify an initial setting for process control variables in an industrial process.

3. A method according to claim 1 which is performed for off-line monitoring and control of process variables.

4. A method according to claim 1 which is performed on-line to monitor and control process variables.

5. A method according to claim 1 in which the image is captured in any selected region of the electromagnetic spectrum.

6. A method according to claim 1 in which the image is a grayscale image.

7. A method according to claim 1 in which the image is captured in the visible spectrum.

8. A method according to claim 1 in which the image is captured in the near infra-red spectrum.

9. A method according to claim 1 in which a multivariate statistical projection method is applied to an image to reduce the dimensions to a low dimensional score space image data defined by a small number of score vectors $t_a$ and said feature vector is created from said low dimensional score space image data.

10. A method according to claim 9 in which said multivariate statistical projection method is selected from the groups comprising: multi-resolution analysis (MRA) based on 2-dimensional wavelet transforms, multivariate image analysis (MIA) based on principal component analysis (PCA), or combinations thereof, Markov Random Field (MRF), Gabor filters, and_variations thereof.

11. A method according to claim 1 applied to optimizing and controlling flotation froth in industrial mineral flotation processes.

12. A method according to claim 11 for controlling froth flotation of zinc concentrate in industrial mineral flotation processes.

13. A method according to claim 11 for controlling froth flotation of copper concentrate in industrial mineral flotation processes.

14. A method according to claim 1 applied to optimizing surface quality of plastic injection molded materials.

15. A method according to claim 1 applied to creating suitable formulations for the production of artificial counter tops.

16. The method of claim 1, wherein the process variables comprise formulation conditions.

* * * * *